United States Patent
Yazicioglu et al.

(10) Patent No.: US 8,862,210 B2
(45) Date of Patent: Oct. 14, 2014

(54) ANALOGUE SIGNAL PROCESSORS

(75) Inventors: Refet Firat Yazicioglu, Leuven (BE); Julien Penders, Liège (BE); Sunyoung Kim, Leuven (BE)

(73) Assignees: IMEC, Leuven (BE); Stichting IMEC Nederland, Eindhoven (NL)

( * ) Notice: Subject to any disclaimer, the term of this patent is extended or adjusted under 35 U.S.C. 154(b) by 1037 days.

(21) Appl. No.: 12/882,120

(22) Filed: Sep. 14, 2010

(65) Prior Publication Data

US 2011/0092834 A1    Apr. 21, 2011

Related U.S. Application Data

(60) Provisional application No. 61/242,299, filed on Sep. 14, 2009, provisional application No. 61/365,296, filed on Jul. 16, 2010.

(30) Foreign Application Priority Data

Feb. 1, 2010 (EP) .................................. 10152299

(51) Int. Cl.

| | | |
|---|---|---|
| A61B 5/0402 | (2006.01) | |
| A61B 5/04 | (2006.01) | |
| A61B 5/053 | (2006.01) | |
| A61B 5/0428 | (2006.01) | |
| A61B 5/00 | (2006.01) | |
| G01R 19/25 | (2006.01) | |
| A61B 5/0476 | (2006.01) | |
| A61B 5/0488 | (2006.01) | |

(52) U.S. Cl.
CPC ........... *A61B 5/7225* (2013.01); *A61B 5/04017* (2013.01); *A61B 5/7228* (2013.01); *A61B 5/7239* (2013.01); *A61B 5/0531* (2013.01); *A61B 5/7221* (2013.01); *A61B 5/7232* (2013.01); *A61B 5/0402* (2013.01); *A61B 5/7207* (2013.01); *A61B 5/0428* (2013.01); *G01R 19/2509* (2013.01); *A61B 5/0476* (2013.01); *A61B 5/0488* (2013.01)
USPC ......................................................... 600/509

(58) Field of Classification Search
CPC .. A61B 5/0402; A61B 5/0428; A61B 5/0531; A61B 5/04017; A61B 5/7207; A61B 5/0476; A61B 5/0488; A61B 5/7228; G01R 19/2509
USPC ................ 600/509, 521; 341/123; 700/73–74
See application file for complete search history.

(56) References Cited

U.S. PATENT DOCUMENTS

| | | | |
|---|---|---|---|
| 729,168 | A | 5/1903 | Henderson |
| 3,667,056 | A | 5/1972 | Allington et al. |

(Continued)

FOREIGN PATENT DOCUMENTS

| | | |
|---|---|---|
| EP | 0540144 | 5/1993 |
| EP | 0884851 | 12/1998 |

(Continued)

OTHER PUBLICATIONS

R.F. Yazicioglu et al., "Ultra-Low-Power Wearable Biopotential Sensor Nodes", 31$^{st}$ Annual International Conference of the IEEE EMBS Minneapolis, Minnesota, USA, pp. 3205-3208, Sep. 2-6, 2009.

(Continued)

*Primary Examiner* — Mark W Brockelman
(74) *Attorney, Agent, or Firm* — Knobbe Martens Olson & Bear LLP

(57) ABSTRACT

An analog signal processor (ASP) application-specific integrated circuit (ASIC) is disclosed. The ACIS can be used for remotely monitoring ECG signals of a subject that has reduced power consumption. In one aspect, the ASIC performs the functions of: ECG signal extraction with high resolution using ECG readout channel, feature extraction using a band-power extraction channel, adaptive sampling the ECG signals using an adaptive sampling analog-to-digital converter, and impedance monitoring for signal integrity using an impedance monitoring channel. These functions enable the development of wireless ECG monitoring systems that have significantly lower power consumption but are more efficient that predecessor systems. In one embodiment, the ASP ASIC consumes 30 μW from a 2V supply with compression provided by adaptive sampling providing large reductions in power consumption of a wireless ECG monitoring system of which the ASP ASIC forms a part.

15 Claims, 34 Drawing Sheets

(56) References Cited

U.S. PATENT DOCUMENTS

| | | | |
|---|---|---|---|
| 4,610,254 | A | 9/1986 | Morgan et al. |
| 4,669,301 | A | 6/1987 | Kratt et al. |
| 5,020,541 | A | 6/1991 | Marriott |
| 5,197,479 | A | 3/1993 | Hubelbank et al. |
| 5,381,803 | A | 1/1995 | Herleikson et al. |
| 6,714,813 | B2 | 3/2004 | Ishigooka et al. |
| 6,821,254 | B2 | 11/2004 | Weil et al. |
| 8,068,905 | B2 | 11/2011 | Freeman et al. |
| 2003/0006782 | A1 | 1/2003 | Shambroom et al. |
| 2007/0060802 | A1 | 3/2007 | Ghevondian et al. |
| 2008/0183098 | A1 | 7/2008 | Denison et al. |
| 2010/0324404 | A1 | 12/2010 | Harrold et al. |

FOREIGN PATENT DOCUMENTS

| | | |
|---|---|---|
| EP | 1754441 A1 | 2/2007 |
| EP | 2086111 | 8/2009 |
| WO | WO 2004/052198 A1 | 6/2004 |
| WO | WO 2008/073528 A1 | 6/2008 |

OTHER PUBLICATIONS

R.F. Yazicioglu et al., "A 200 µW Eight-Channel EEG Acquisition ASIC for Ambulatory EEG Systems", IEEE Journal of Solid-State Circuits, vol. 43, No. 12, pp. 3025-3038, Dec. 2008.

A.-T. Avestruz et al,. "A 5 µW/Channel Spectral Analysis IC for Chronic Bidirectional Brain-Machine Interfaces", IEEE Journal of Solid-State Circuits, vol. 43, No. 12, pp. 3006-3024, Dec. 2008.

C.C. Enz et al., "Circuit Techniques for Reducing the Effects of Opamp Imperfections", Proc. of IEEE, vol. 84, No. 11, pp. 1584-1614, Nov. 1996.

R.R. Harrison et al., "A Low-Power Low-Noise CMOS Amplifier for Neural Recording Applications", IEEE J. Solid State Circuits, vol. 38, No. 6, pp. 958-965, Jun. 2003.

J. Ottenbacher et al., "Reliable Motion Artifact Detection for ECG Monitoring Systems with Dry Electrodes", IEEE EMBS Conf., pp. 1695-1698, Aug. 2008.

X.D. Zou et al., "A 1V 450nW Fully Integrated Programmable Biomedical Sensor Interface System", IEEE J. of Solid-State Circuits, vol. 44, No. 4, pp. 1067-1077, Apr. 2009.

ANSI/AAMI-EC13, "American national standards for cardiac monitors, hearth rate meters and alarms", Association for the Advancement of Medical Instrumentation, 2002.

B. Gyselinckx et al., "Human++: Energing Technology for Body Area Networks", Very Large Scale Integration, 2006 IFIP International Conference, pp. 175-180, Oct. 2006.

J. Penders et al., "Human++: from Technology to Emerging Health Monitorning Concepts", Proceedings of the 5$^{th}$ International Workshop on Wearable and Implantable Body Sensor Networks, pp. 94-98, Jun. 1-3, 2008.

R.F. Yazicioglu et al., "A 60µW 60nV/√Hz Readout Front-end for Portable Biopotential Acquisition Systems", IEEE J. Solid-State Circuits, vol. 42, No. 5, pp. 110-1110, May 2007.

C Enz., "A CMOS Chopper Amplifier", IEEE J. Solid-State Circuits, vol. 22, No. 3, pp. 335-342, Jun. 1987.

MSJ Steyaert et al., "A Micropower Low-Noise Monolithic Instrumentation Amplifier for Medical Purposes", IEEE J. Solid-State Circuits, vol. sc-22, No. 6, lines 1163 to 1168, Dec. 1987.

I Romero et al., "Low-Power Robust Beat Detection in Ambulatory Cardiac Monitoring", IEEE BioCAS, pp. 249-252, Nov. 2009.

H. Tam et al., "Minimizing Electrode Motion Artifact by Skin Abrasion", IEEE Trans. on Biomedical Engineering, vol. BME-24, pp. 134-139, 1977.

M Trakimas et al., "A 0.8V Asynchronous ADC for Energy Constrained Sensing Application", IEEE CICC, pp. 173-176, Sep. 2008.

Jalaleddine et al., "ECG data compression techniques—A unified approach", IEEE trans on Biomed. Eng., vol. 37, No. 4, Apr. 1990.

Kalinin et al., "A simple method to adapt time sampling of the analog signal", Nuclear Instruments and Methods in Physics Research A 524 (2004), pp. 374-376.

H. Kim et al., "A Low Cost Quadratic Level ECG Compression Algorithm and Its Hardware Optimization for Body Sensor Network System", IEEE EMBS 2008, pp. 5490-5493, Aug. 2008.

Extended European Search Report for European Patent Application No. 10176687.1-1265 dated Nov. 21, 2011.

Bohs L N et al., "Real-time adaptive sampling with the fan algorithm", Medical and Biological Engineering and Computing, Springer, Heildelberg, DE, vol. 26, No. 6, Nov. 1, 1988, pp. 563-573.

Barr et al., "Adaptive sampling of cardiac waveforms", Journal of Electrocardiology, Elsevier Science, vol. 21, Jan. 1, 1988, pp. S57-S60.

Rieger R et al., "An Adaptive Sampling System for Sensor Nodes in Body Area Networks", IEEE Transactions of Neural Systems and Rehabilitation Engineering, IEEE Service Center, New York, NY, US, vol. 17, No. 2, Apr. 1, 2009, pp. 183-189.

Bohs L N et al., "Prototype for real-time adaptive sampling using the fan algorithm" , Medical and Biological Engineering and Computing, Springer, Heildelberg, DE, vol. 26, No. 6, Nov. 1, 1988, pp. 574-583.

Rieger R. et al., "A Signal Based Clocking Scheme for A/D Converters in Body Sensor Networks", Tencon 2006. 2006 IEEE Region 10 Conference, IEEE, PI, Nov. 14, 2006, pp. 1-4.

Extended European search report for European Patent Application No. 10176639.2-1265 dated Dec. 23, 2010 by European Patent Office.

US Office Action for U.S. Appl. No. 12/882,126 mailed Jul. 3, 2012 by the U.S. Patent and Trademark Office.

ANALOGUE SIGNAL PROCESSORS

CROSS REFERENCE TO RELATED APPLICATIONS

This application claims priority under 35 U.S.C. §119(e) to U.S. provisional patent application 61/242,299 filed on Sep. 14, 2009 and U.S. provisional patent application 61/365,296 filed on Jul. 16, 2010. This application is related to U.S. application Ser. No. 12/882,126, filed on the same day herewith and issued as U.S. Pat. No. 8,454,505 on Jun. 4, 2013, and titled "METHOD AND ELECTRONIC MEDICAL DEVICE FOR SIMULTANEOUSLY MEASURING AN IMPEDANCE AND A BIOPOTENTIAL SIGNAL," and U.S. application Ser. No. 12/882,118, filed on the same day herewith and titled "ADAPTIVE SAMPLING." Each of the above applications is hereby incorporated by reference in its entirety.

BACKGROUND OF THE INVENTION

1. Field of the Invention

The present disclosure relates to analogue signal processors and is more particularly, although not exclusively concerned with the analogue signal processors that can be used for the monitoring of biopotential signals.

2. Description of the Related Technology

The ever-increasing cost of healthcare creates a major challenge to provide more efficiently high-quality care for an increasing number of patients using limited financial and human resources. This leads a drive towards personal 'telehealth' systems including remote monitoring and management that requires the development of smart biopotential monitoring systems with stringent size and power autonomy constraints.

An example of such a system is described in the article entitled "Human++: Emerging Technology for Body Area Networks" by B Gyselinckx, R Vullers, C Hoof, J Ryckaert, R F Yazicioglu, P Fiorini and V Leonov, Very Large Scale Integration, 2006 IFIP International Conference, October 2006, pages 175 to 180.

Among these biopotential monitoring systems, the ambulatory monitoring of ECG signals is gaining significant interest over the recent years.

The use of health monitoring systems is also described in "Human++: from Technology to Emerging Health Monitoring Concepts" by J Penders, B Gyselinckx, R Vullers, M De Nil, S Nimmala, J van de Molengraft, R F Yazicioglu, T Torfs, V Leonov, P Merken and C Van Hoof, Proceedings of the 5th International Workshop on Wearable and Implantable Body Sensor Networks, pages 94 to 98, 1 to 3 Jun. 2008.

SUMMARY OF CERTAIN INVENTIVE ASPECTS

In accordance with one aspect of the present disclosure, there is provided an application-specific integrated circuit for cardiac monitoring, the circuit comprising: —an electrocardiogram readout channel having an input and an output, the input being arranged to receive a monitored signal and the output providing a electrocardiogram signal; and an adaptive sampling unit for sampling the electrocardiogram signal; characterized in that the adaptive sampling unit includes an adaptive threshold generation unit that generates a threshold value used to control the adaptive sampling unit.

Additionally, the adaptive sampling unit further comprises an activity detector that includes the adaptive threshold generation unit.

The application-specific integrated circuit may further comprise a band-power extraction channel that extracts power information from the monitored signal as well as an impedance readout channel that extracts impedance information from the monitored signal.

A stimulation current generator may also be provided for a device of which the circuit forms a part. The stimulation current generator preferably comprises chopper stabilized AC sources.

The application-specific integrated circuit also comprises at least one input stage for providing the monitored signal to at least the electrocardiogram channel. In an embodiment, one input stage is provided for both the electrocardiogram channel and the band-power extraction channel. An additional input stage is provided for the impedance readout channel.

The application-specific integrated circuit further comprises at least one output stage, one for the electrocardiogram channel, two for the band-power extraction channel and two for the impedance readout channel—one for each of the imaginary and real components output by each of the band-power extraction channel and the impedance readout channel.

In an embodiment, both the input and output stages comprise instrumentation amplifiers.

Additionally, two low frequency oscillators and one high frequency oscillator is provided, together with a bias circuit generator, configuration registers and a digital control circuit.

It is preferred that the adaptive sampling unit comprises an analogue-to-digital converter so that only electrocardiogram signals are sampled at a high frequency and digitized for further processing.

In accordance with another aspect of the present disclosure there is provided a medical monitoring device comprising: —an application-specific integrated circuit as described above; a digital controller for processing signals output by the application-specific integrated circuit and for providing control signals to the application-specific integrated circuit; and a wireless module for receiving data from the digital controller and for transmitting it to a network.

In accordance with a further aspect of the present disclosure, there is provided a wireless electrocardiogram monitoring system comprising: —a network; and a medical monitoring device as described above, the wireless module of the medical monitoring device transmitting data to the network.

In one embodiment of the present disclosure, there is provided a method for operating a medical monitoring device as described above, the method comprising the steps of: —determining a change in an impedance measurement in an electrocardiogram signal with respect to a predetermined threshold value; and activating processing activities of the device. The processing activities of the device are activated when the impedance measurement falls below the predetermined threshold value, and are deactivated when the impedance measurement rises above the predetermined threshold value.

In another embodiment of the present disclosure, there is provided a method for transferring data from a medical monitoring device as described above, the method comprising: determining an adaptively sampled ECG signal; processing the adaptively sampled ECG signal to extract features therefrom; and transmitting data relating to the extracted features to a host network. The data may be transferred continuously, or transferred when a disorder is detected in the extracted features. In either case, the data may also be stored within the medical monitoring device.

In a further embodiment of the present disclosure, there is provided a method for simultaneously retrieving data from a medical monitoring device described above, the method comprising: deriving an electrocardiogram signal; and deriving at least band-power measurements from the derived electrocardiogram signal. The derived band-power measurements may be used for beat detection. In this case, a low-power beat detection algorithm is used.

Additionally, the method further comprises the step of deriving impedance measurements from the derived electrocardiogram signal. The derived impedance measurements may be used to remove artifacts from the derived electrocardiogram signal to provide a compensated electrocardiogram signal that can be used for beat detection.

The derived impedance measurements may also be used for detecting the presence of artifacts. If no artifacts are detected, the derived band-power measurements may be used for beat detection. If artifacts are detected, the derived electrocardiogram signal may be used for beat detection. In this case, a precision beat detection algorithm is used.

Moreover, RR intervals, the distance between peaks in an electrocardiogram signal, may be determined from the derived impedance measurements. If the RR intervals are not consistent, the electrocardiogram signal is used for beat detection instead of the band-power measurements.

BRIEF DESCRIPTION OF THE DRAWINGS

For a better understanding of the present disclosure, reference will now be made, by way of example only, to the accompanying drawings in which.

DETAILED DESCRIPTION OF CERTAIN ILLUSTRATIVE EMBODIMENTS

Figure 1:
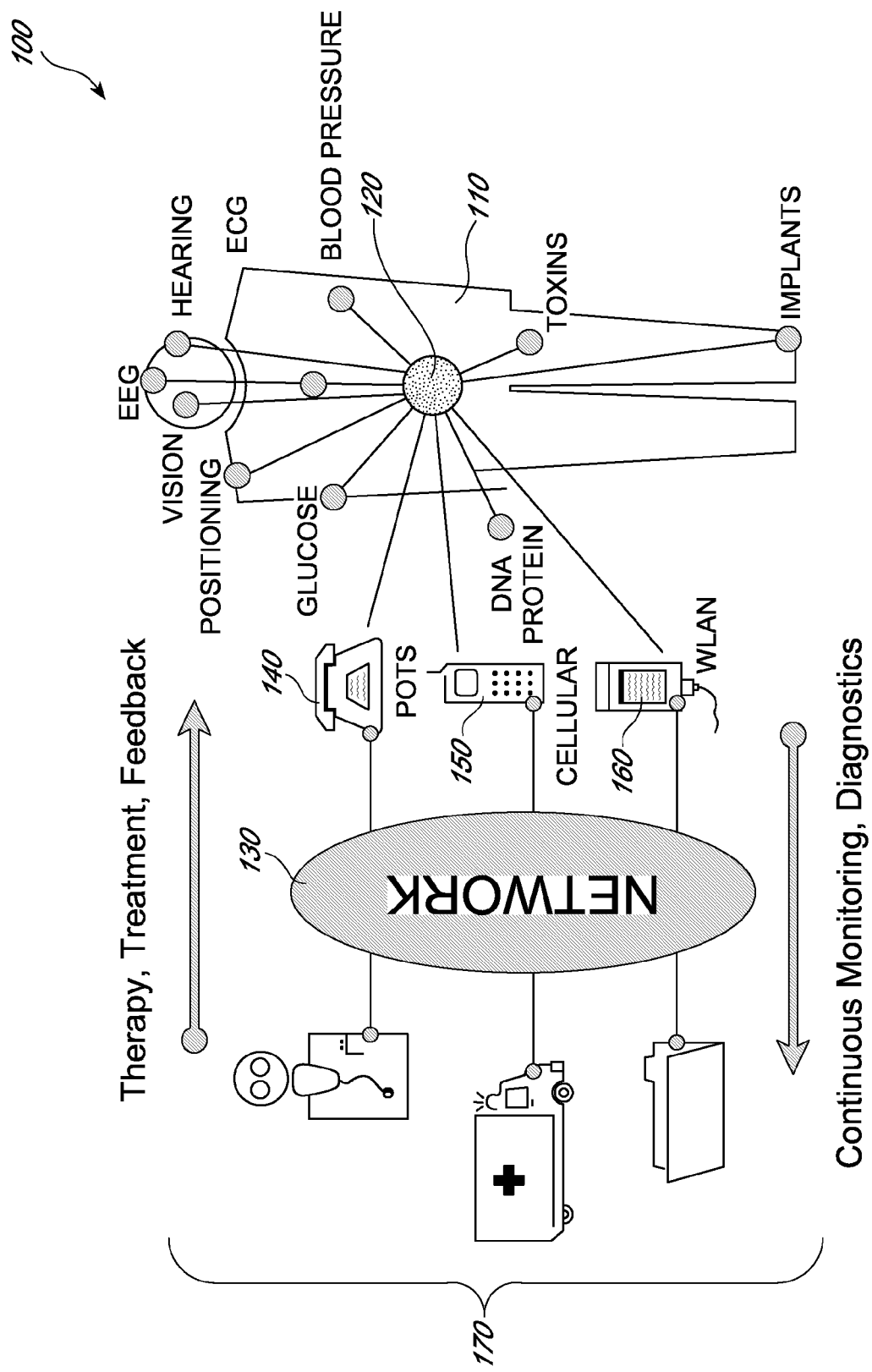
FIG. 1 illustrates 'connected healthcare' as envisaged by medical trends.

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes.

Certain embodiments relate to analogue signal processors and is more particularly, to analogue signal processors that can be used for the monitoring of biopotential signals.

In certain embodiments, the key requirements for such systems are the extraction, analysis and wireless transmission of electrocardiogram (ECG) signals with low-power consumption, and robust operation under the presence of signal artifacts. However, the power breakdown of existing systems shows that digital signal processing (DSP) and wireless data transmission dominates the system power consumption, increasing the significance of research on ultra-low-power DSP and radio or wireless platforms.

In each of the systems described above, there is a need for a signal processor that handles the monitored signals effectively and efficiently without increasing the power consumption of the system. In one embodiment, the system provides an ASP ASIC that comprises building blocks essential to cardiac monitoring.

In accordance with one embodiment, the ASP ASIC extracts ECG signals with high signal quality, assists DSP platforms for low-power signal analysis and data compression, and monitors the signal integrity of the ECG signal extraction whilst enabling a significant reduction in power consumption of the system.

Referring initially to FIG. 1, a 'connected healthcare' system 100 is shown that provides a vision for future healthcare systems utilizing miniature and smart sensor nodes for extracting key medical information. Currently, the power dissipation of these sensor nodes is dominated by digital signal processing and wireless data transmission.

A patient 110 wears a monitor 120 that can monitor vital signs, for example, electroencephalogram (EEG) signals, vision, hearing, ECG signals, blood pressure, glucose levels, DNA protein, positioning, toxins and implants. The monitor 120 communicates with a network 130 transmitting signals relating to the patient's vital signs. The network may be connected by a standard telephone landline 140, by cellular telephone 150 or by a wireless local area network (WLAN) 160. The network 130 monitors the signals and interacts with doctors, medical assistance and patient records, shown generally as 170, to provide continuous monitoring and diagnostics that can be used for therapy, treatment and/or feedback for the patient 110.

Figure 2:
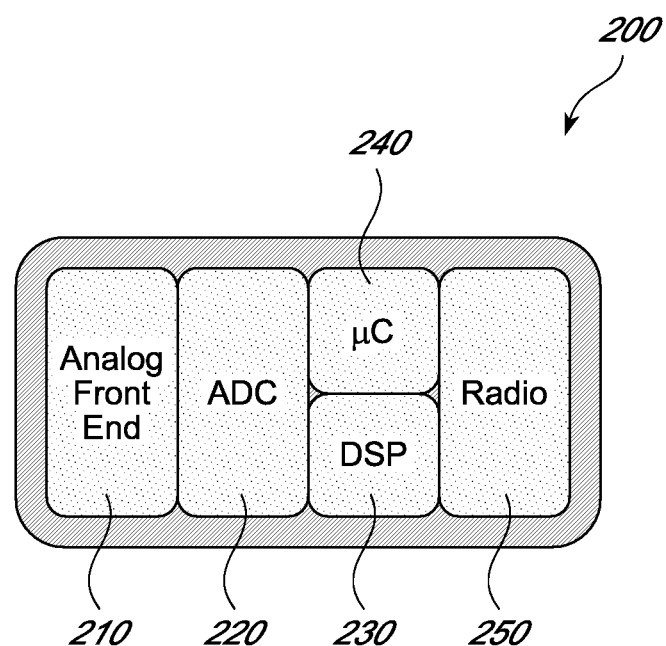
FIG. 2 illustrates a block diagram of components of a monitoring device for use in 'connected healthcare' shown in FIG. 1.

FIG. 2 illustrates a monitor 200 that can be used to collect data relating to a patient's vital signs and to transmit the data to a network. The monitor 200 comprises an analogue front end 210, an ADC 220, a DSP 230, a microcontroller 240 and a radio or wireless link 250. The analogue front end 210 collects data from the patient which is sampled and digitized by the ADC 220 before further processing in the DSP 230. The processed data is then passed to the radio or wireless link 250 for transmission to a remote monitoring centre (not shown). The microcontroller 240 controls the operation of the DSP 230 and the radio or wireless link 250. The power dissipation in each of the three main elements is typically, r a total power dissipation of approximately 2 mW: the radio or wireless link dissipates around 73%, the DSP 25% and the analogue front end 2%.

Figure 3:
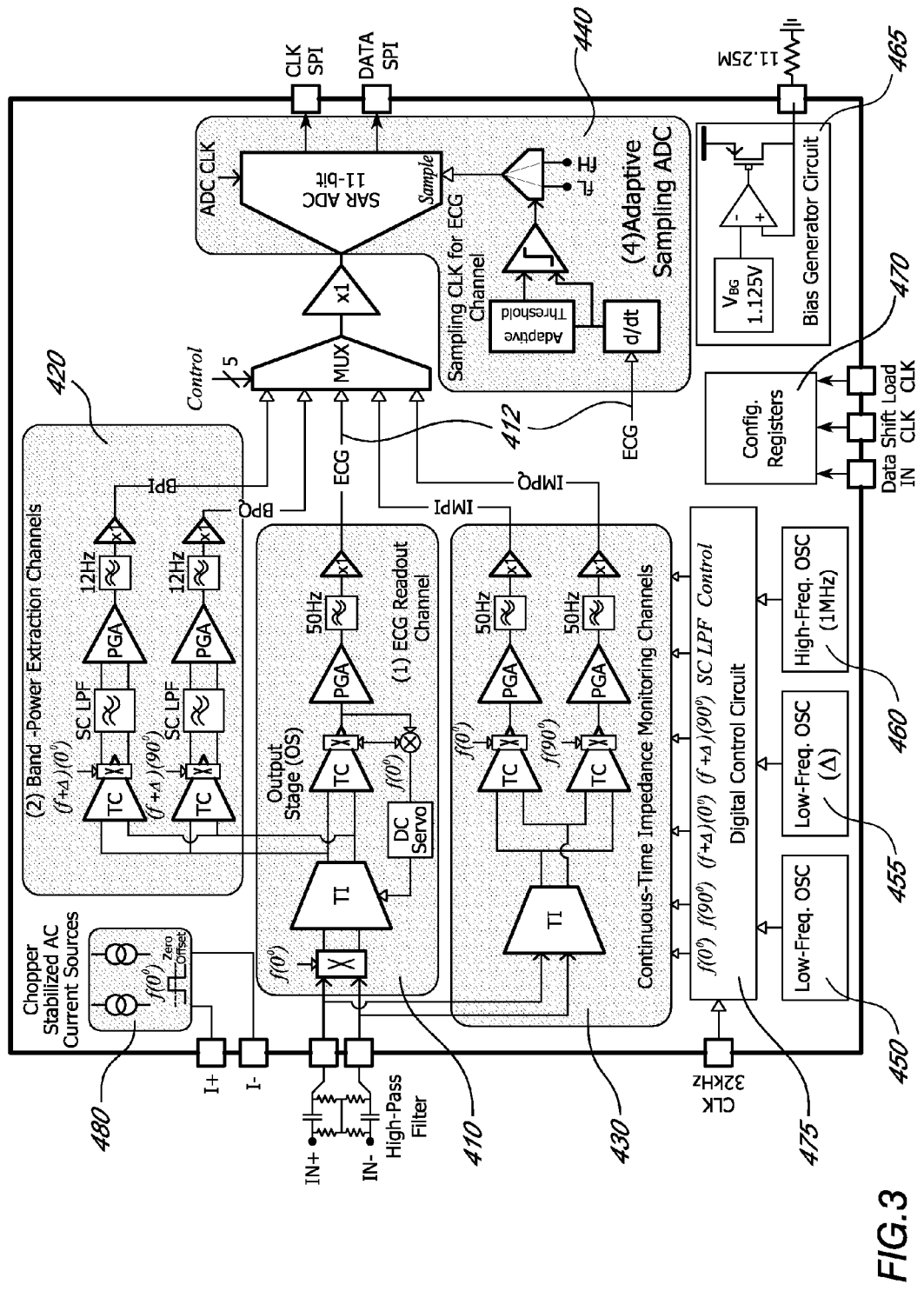
FIG. 3 illustrates an architecture for an analogue signal processor (ASP) application-specific integrated circuit (ASIC) in accordance with one embodiment.

FIG. 3 illustrates the operation of an ASP 400 in accordance with one embodiment. The ASP 400 comprises four main building blocks, namely, a low noise and high common mode rejection ratio (CMRR) readout channel 410, two band-power extraction channels 420, an impedance readout circuit 430 and an adaptive sampling (AS) ADC 440. The CMRR readout channel 410 extracts ECG signals. The power extraction channels 420 extract signal fluctuations in a specified frequency band. The impedance readout circuit 430 monitors electrode-tissue contact impedance at the same time as the biopotential signals, for example, the ECG signals are being monitored. The AS-ADC 440 reduces the equivalent data rate of the ECG readout channel 410.

In addition to the four main building blocks, the ASP 400 also includes two low frequency oscillators 450, 455, a high frequency oscillator 460, a bias circuit generator 465 and configuration registers 470. The low frequency oscillators 450, 455 operate at 8 kHz and the high frequency oscillator 460 operates at 1 MHz.

The oscillators 450, 455, 460 provide inputs for a digital control circuit 475. The digital control circuit 475 supplies frequency and control signals for the ECG readout channel 410, the band power extraction channels 420 and the impedance readout circuit 430 as shown.

The operation of the ASP 400 is as follows: the ECG readout channel 410 extracts the biopotential signals as an ECG signal 412 that is compressively sampled by the AS-ADC 440. This minimizes the equivalent output data rate of the ASP output which in turn reduces the power consumption of the DSP and radio or wireless data transmission (FIG. 2). The band power extraction channels 420 implement a band-pass filter for extracting signal fluctuations in the selected or specified frequency band. This enables the detection of ECG signal features with very low power consumption. This has been described in "A 60 μW 60 nV√Hz Readout Front-end for Portable Biopotential Acquisition Systems" by R F Yazicioglu, P Merken, R Puers and C Van Hoof, IEEE J. Solid-State Circuits, vol. 42, no. 5, pages 110 to 1110, May 2007, which is incorporated herein by reference.

The ASP 400 also includes a current stimulation block 480 that stimulates an electrode-tissue interface (not shown) with an AC current. The resulting voltage is amplified by the impedance readout circuit 430 to extract imaginary and real components of the electrode-tissue impedance. This enables the system to monitor continuously the ECG signal integrity against lead connectivity and motion-induced signal artifacts.

The sampling frequencies for signal components in the ASP 400 can be as shown in Table 1 below.

TABLE 1

| Signal component | Sampling frequency (Hz) |
| --- | --- |
| Band power imaginary | 64 |
| Band power real | 64 |
| Impedance imaginary | 250 |
| Impedance real | 250 |
| ECG | 64 or 1024 (adaptive sampling) |

Figure 4:
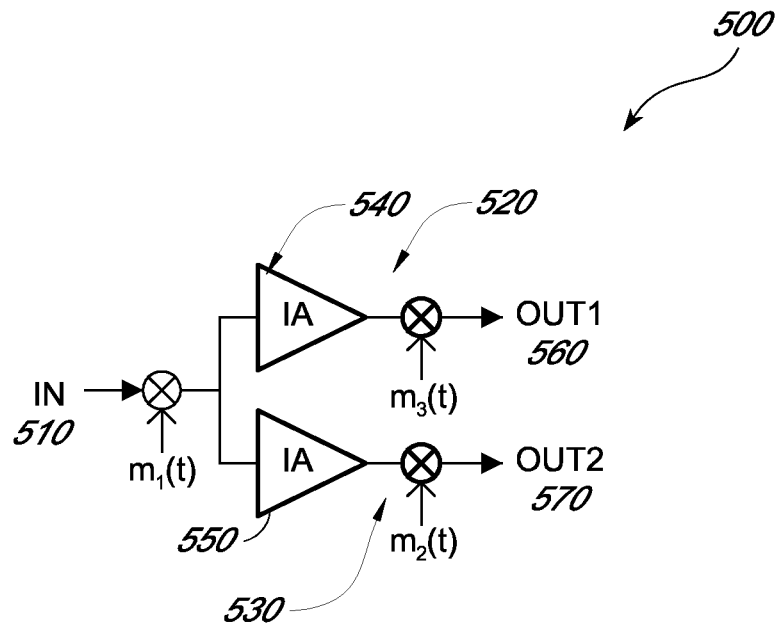
FIG. 4 illustrates a conventional architecture requiring two signal paths requiring different demodulator frequency or phase, gain, and/or bandwidth.

It is known, for example, from "A CMOS Chopper Amplifier" by C Enz, E Vittoz and F Krummenacher, IEEE J. Solid-State Circuits, vol. 22, no. 3, pages 335 to 342, June 1987, which is incorporated herein by reference, that the use of chopper modulation can enable the implementation of low-noise and low-power IAs for the extraction of biopotential signals. In addition to "A 60 μW 60 nV√Hz Readout Front-end for Portable Biopotential Acquisition Systems" mentioned above, the use of IAs has also be described in "A 200 μW Eight-Channel EEG Acquisition ASIC for Ambulatory EEG Systems" by R F Yazicioglu, P Merken, R Puers and C Van Hoof, IEEE J. Solid-State Circuits, vol. 43, no. 12, pages 3025 to 3038, December 2008, which is incorporated herein by reference. However, the use of parallel signal paths, while employing chopper modulation, requires the use of a single IA for each signal path as shown in FIG. 4 and described in "A 5 μW/Channel Spectral Analysis IC for Chronic Bidirectional Brain-Machine Interfaces" by A-T Avestruz, W Santa, D Carlson, R Jensen, S Stanslaski, A Helfenstine and T Denison, IEEE J. Solid-State Circuits, vol. 43, no. 12, pages 3006 to 3024, December 2008, which is incorporated herein by reference.

In FIG. 4, an arrangement 500 is shown in which an input signal 510 is divided into two signal paths 520, 530. Each signal path 520, 530 has an associated IA 540, 550 for providing respective output signals 560, 570. Whilst this arrangement enables flexible and independent demodulation for each signal path 520, 530, there is an associated increase in the overall power consumption.

Figure 5:
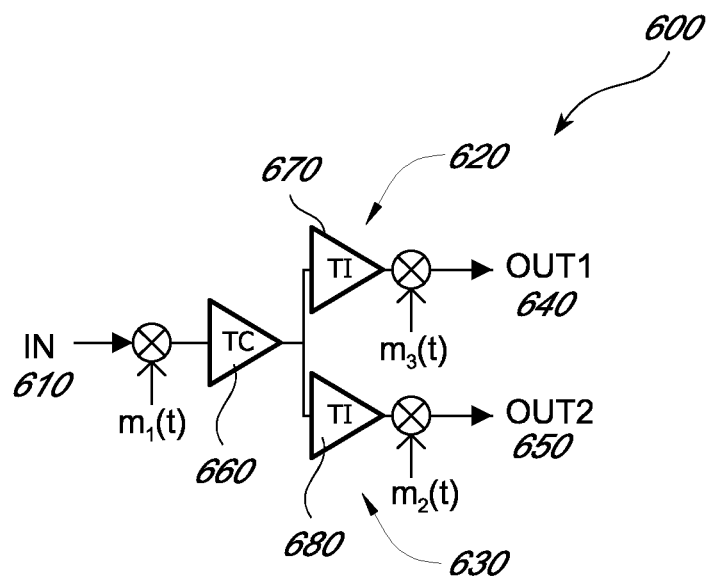
FIG. 5 illustrates a new architecture in accordance with one embodiment in which a single input stage is utilized with multiple output stages.

FIG. 5 illustrates a chopper modulated IA 600 that provides good trade-off between power dissipation and architectural flexibility for the implementation of different functionalities. In the IA 600, a single input signal 610 is divided into two signal paths 620, 630 as shown. This IA 600 provides two output signals 640, 650 without the need for an IA in each signal path 620, 630. The chopper modulated IA 600 includes a transconductance (TC) input stage 660 that drives two output transimpedance (TI) stages 670, 680. Whilst only two output TI stages 670, 680 are shown, it will be appreciated that more than two such stages may be driven from a single TC input stage 660.

A chopper modulator is inserted before the input stage and the demodulators can be included in the output stages. This isolates the different output stages and allows the implementation of independent signal paths that are tailored to extract different properties of the same input signal. On the other hand, reducing the number of IA input stages minimizes the contribution of the IA to the total power consumption of the ASP ASIC (FIG. 3).

Table 2 below compares target specifications for the ASP ASIC shown in FIG. 3 with the standards specifications.

TABLE 2

|  | ANSI/AAM-EC13 standards | Target specifications |
|---|---|---|
| Operating voltage | — | 2 V |
| Gain | — | 100 |
| Input dynamic range | ±5 mV | ±5 mV |
| Input referred noise | <60 µVpp | <10 µVpp (<100 nV/√Hz over 150 Hz) |
| Input impedance | >2.5 MΩ | >10 MΩ |
| CMRR | >80 dB | >100 dB |
| Electrode offset filtering range | >±300 mV | >±300 mV |

An architecture and design of the IA according to the specifications given in Table 2 will now be described.

Figure 6:
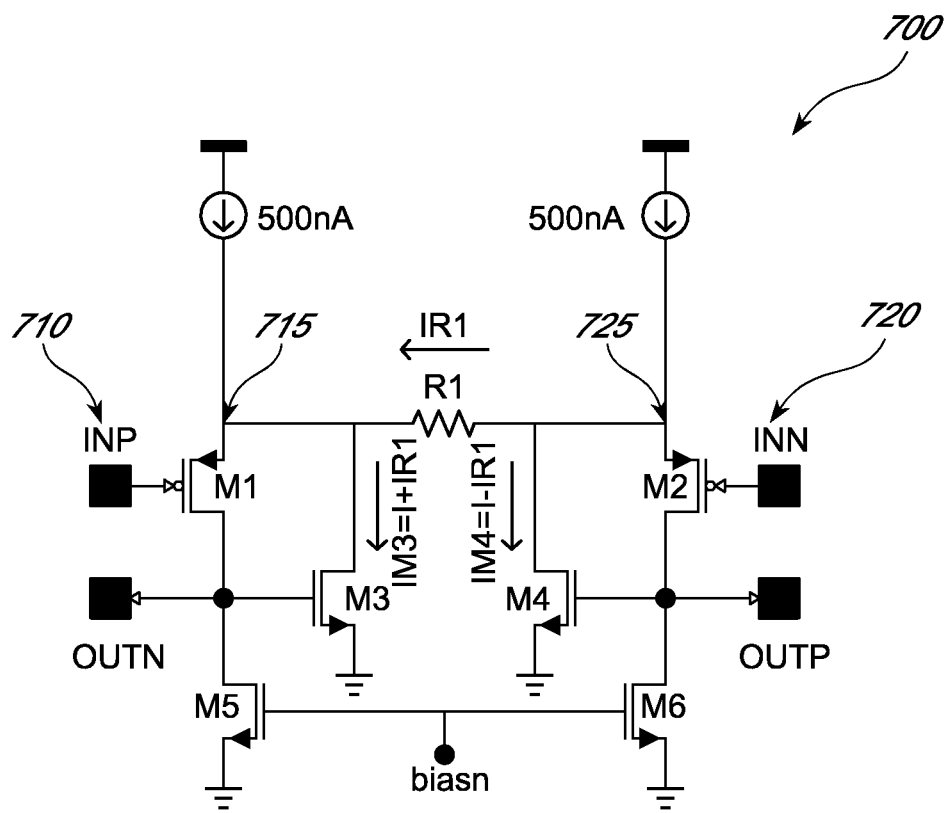
FIG. 6 illustrates an architecture of a transconductance stage that implements the input stage of an instrumentation amplifier (IA)

In FIG. 6, an architecture of an input TC stage 700 is shown. This stage 700 is equivalent to the TC stage 660 shown in FIG. 5. An input differential signal 710, 720 is copied to terminals 715, 725 of resistor $R_1$. The current, $I_{R1}$, deflects the currents of transistors M3 and M4 by the same amount. Hence the TC of the input stage can be written as:

$$TC = \frac{I_{OUT}}{V_{IN}} = \frac{I_{M3} - I_{M4}}{V_{IN}} = \left[\frac{1}{\frac{R_1}{2} + \frac{1}{gm_1 gm_3 R_{out,M_{5,6}}}}\right] \cong \frac{2}{R_1} \quad (1)$$

where
$I_{OUT}$ is the output current
$V_{IN}$ is the input voltage
$I_{M3}$ is the current flowing through transistor M3
$I_{M4}$ is the current flowing through transistor M4
$R_1$ is the value of resistor $R_1$
$gm_1$ is the gain of transistor M1
$gm_3$ is the gain of transistor M3
and $R_{out,M_{5,6}}$ is the output resistance at transistors M5, M6

Figure 7:
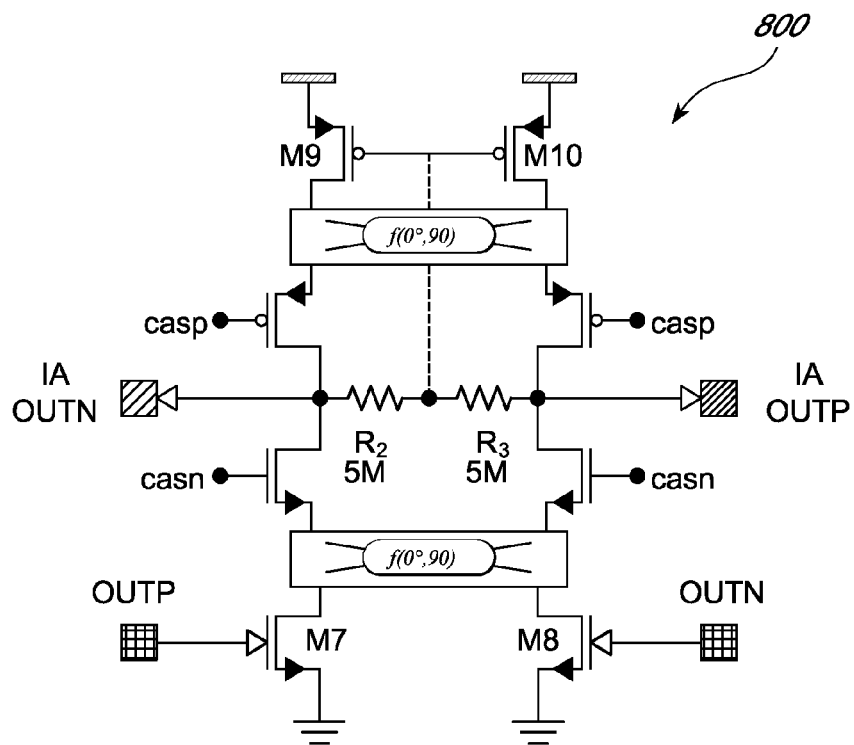
FIG. 7 illustrates an architecture for a fully differential transimpedance (TI) output stage.
Figure 8:
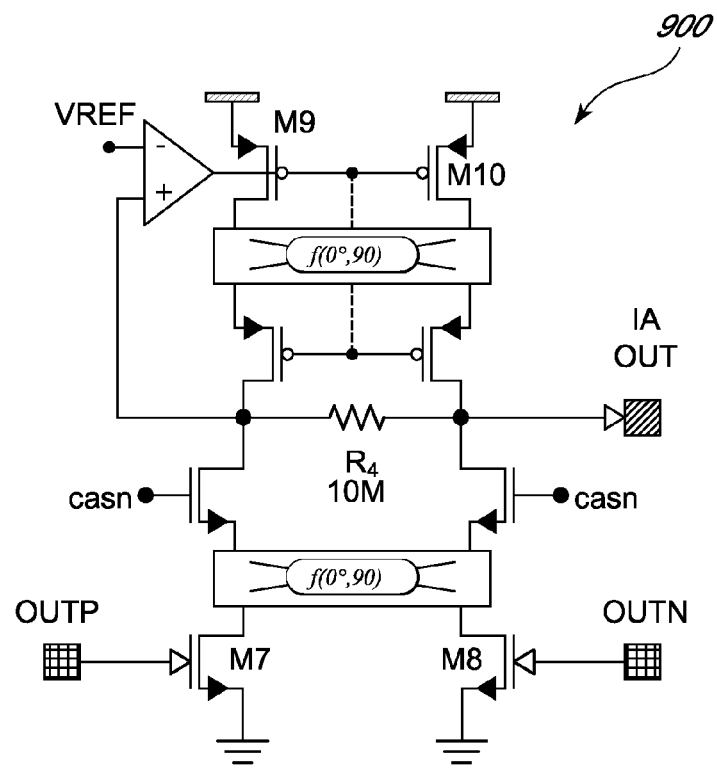
FIG. 8 illustrates an architecture for a single-ended transimpedance (TI) output stage.

FIG. 7 illustrates an architecture of a fully-differential TI output stage 800, and FIG. 8 illustrates an architecture of a single-ended TI output stage 900.

Current from a TC input stage (FIG. 6) is converted into voltage by copying the current through transistors M3 and M4 (FIG. 6) to the differential branches of the output TI stages 800, 900 by using replica transistors M7 and M8. Transistors M9 and M10 force an equivalent current through the branches of the output TI stage 800, 900. This causes half the current difference between M7 and M8 to flow through load resistors $R_{load}$, that is, $R_2+R_3$ in FIG. 7 and $R_4$ in FIG. 8. As a result, the TI of the output stages 800, 900 can be written as:—

$$TI = \frac{V_{OUT}}{I_{IN}} = \frac{V_{OUT}}{I_{M7} - I_{M8}} = \frac{[R_{load} \| R_{out}]}{2} \cong \frac{R_{load}}{2} \quad (2)$$

where
$V_{OUT}$ is the output voltage
$I_{IN}$ is the input current
$I_{M7}$ is the current flowing through transistor M7
$I_{M8}$ is the current flowing through transistor M8
$R_{load}$ is the value of load resistor $R_{load}$
and $R_{out}$ is the value of the output impedance of the cascade output transistor stages Combining equations (1) and (2), the gain of the IA can be written as:

$$Av_{IA} = TC \times TI \cong \frac{R_{load}}{R_1} \quad (3)$$

where $R_1$ has a value of 100 kΩ and $R_{load}$ has a value of 10 MΩ.

This sets the gain of the IA to 100.

Figure 9:
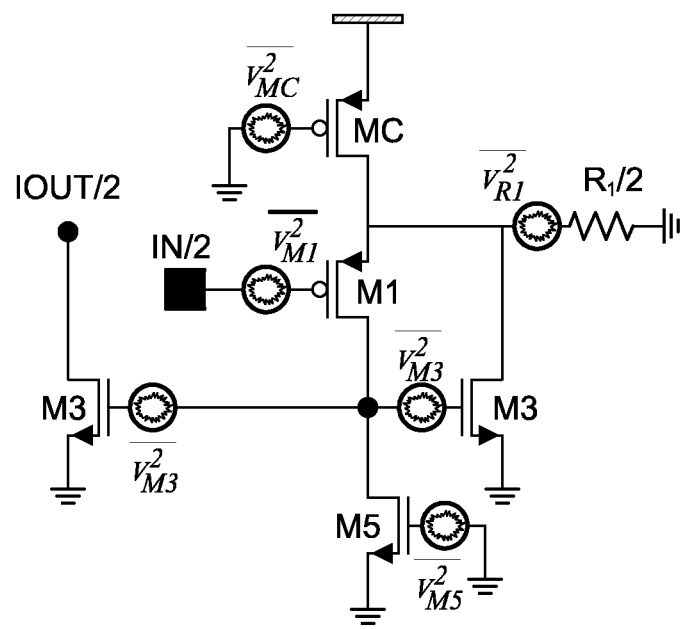
FIG. 9 illustrates an equivalent half circuit of the IA input stage for noise calculations.

The input stage of the IA dominates the total input referred noise. FIG. 9 shows an equivalent noise model of the input stage half-current. From nodal analysis, the input referred contribution of each noise source in the half-circuit can be expressed as:

$$\overline{v_{IN}^2} = \quad (4)$$
$$2\overline{v_{M1}^2} + \overline{v_{R_1}^2} + 2gm_c^2 R_1^2 \overline{v_{MC}^2} + 4gm_3^2 R_1^2 \overline{v_{M3}^2} + 2gm_5^2\left(\frac{2}{gm_1} + R_1\right)^2 \overline{v_{M5}^2}$$

Equation (4) indicates that the noise and respective power consumption can be optimized by forcing the transistors MC, M3 and M5 to operate in strong inversion.

The input dynamic range (DR) of the IA is defined by the quiescent current flowing through the transistors M3 and M4 and by the resistor $R_1$ as:

$$DR = \pm I_{M3,M4} R_1 \quad (5)$$

The design consideration for the input DR is according to Table 2 above. Hence, the currents through $I_{M3,M4}$ is set to 175 nA which corresponds to an input DR of ±17.5 mV for $R_1$=100 kΩ.

According to Table 2 above, the IAs for the extraction of ECG signals should be capable of rejecting ±300 mV DC polarization voltage (PV) from the biopotential electrodes. Architectures that can implement such DC headroom without using off-the-shelf components lead to lower performance IAs are known in the art. On the other hand, the use of conventional off-chip high-pass filters significantly reduces the input impedance, where especially the common mode input impedance is very important for achieving high CMRR under the influence of large electrode impedance is also known in the art.

Figure 10:
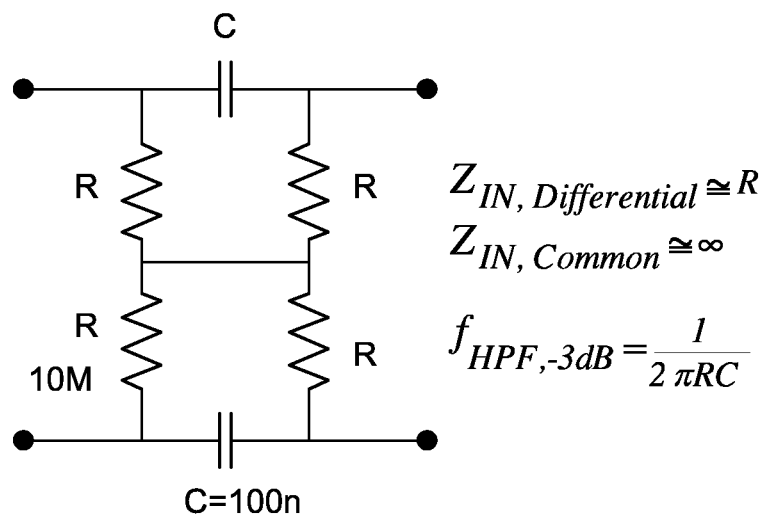
FIG. 10 illustrates a schematic diagram of a floating high-pass filter.

In view of this, the implemented IA uses a floating high-pass filter as shown in FIG. 10. The main advantage of using a floating high-pass filter compared to conventional passive high-pass filters is the elimination of the grounded resistor, thereby implementing very large common mode input impedance. This is specifically important to sustain the CMRR of the system under large electrode impedance mismatches.

The resistors are used before the capacitors to sense the average DC potential of the input leads. This is set by a ground electrode described below with reference to FIG. 27 below. The common mode input impedance is only defined by parasitic capacitances.

Figure 11:
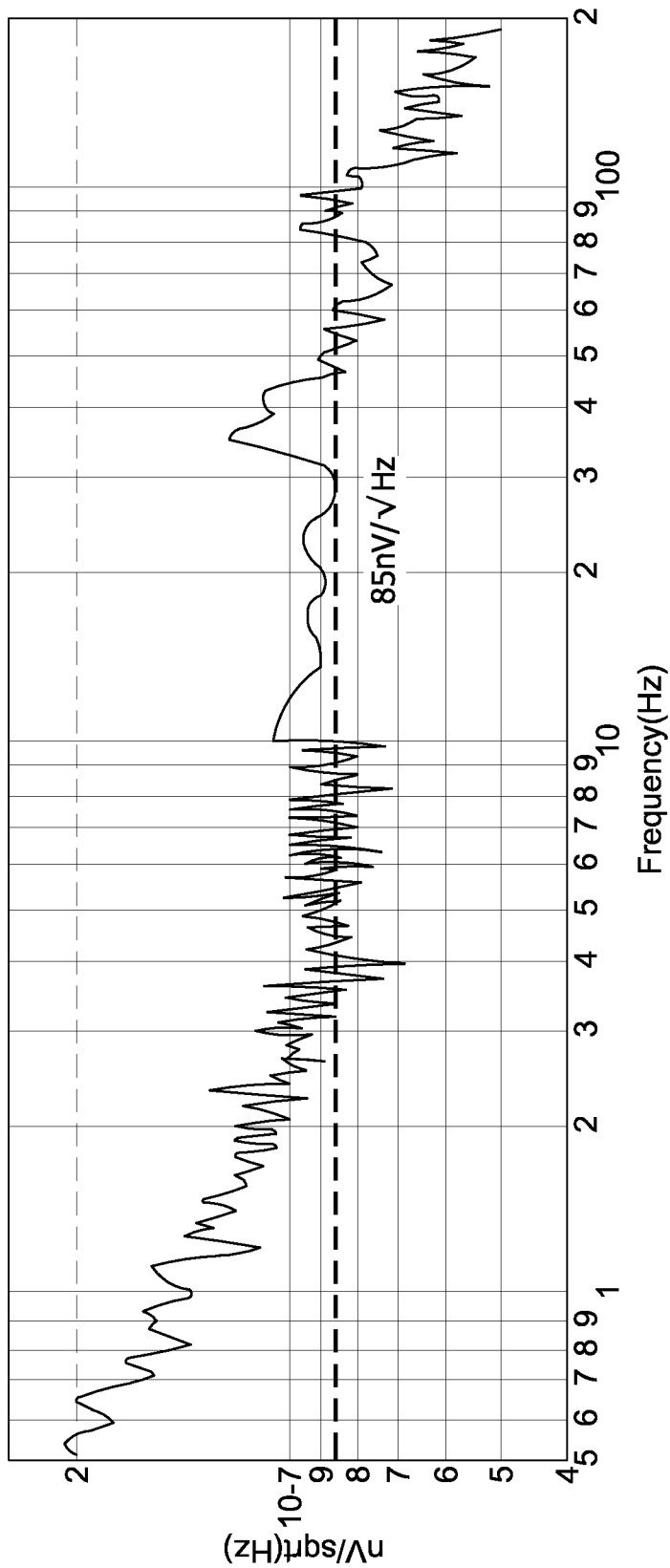
FIG. 11 illustrates input referred noise measurement of the IA of FIG. 6.

The characterization of the IA is performed at the output of the ECG readout channel. FIG. 11 shows that the measured input-referred noise of the IA is 85 nV$_{rms}$/√Hz, mainly dominated by the input transistors M1 and M2, and the resistor R$_1$.

Figure 12:
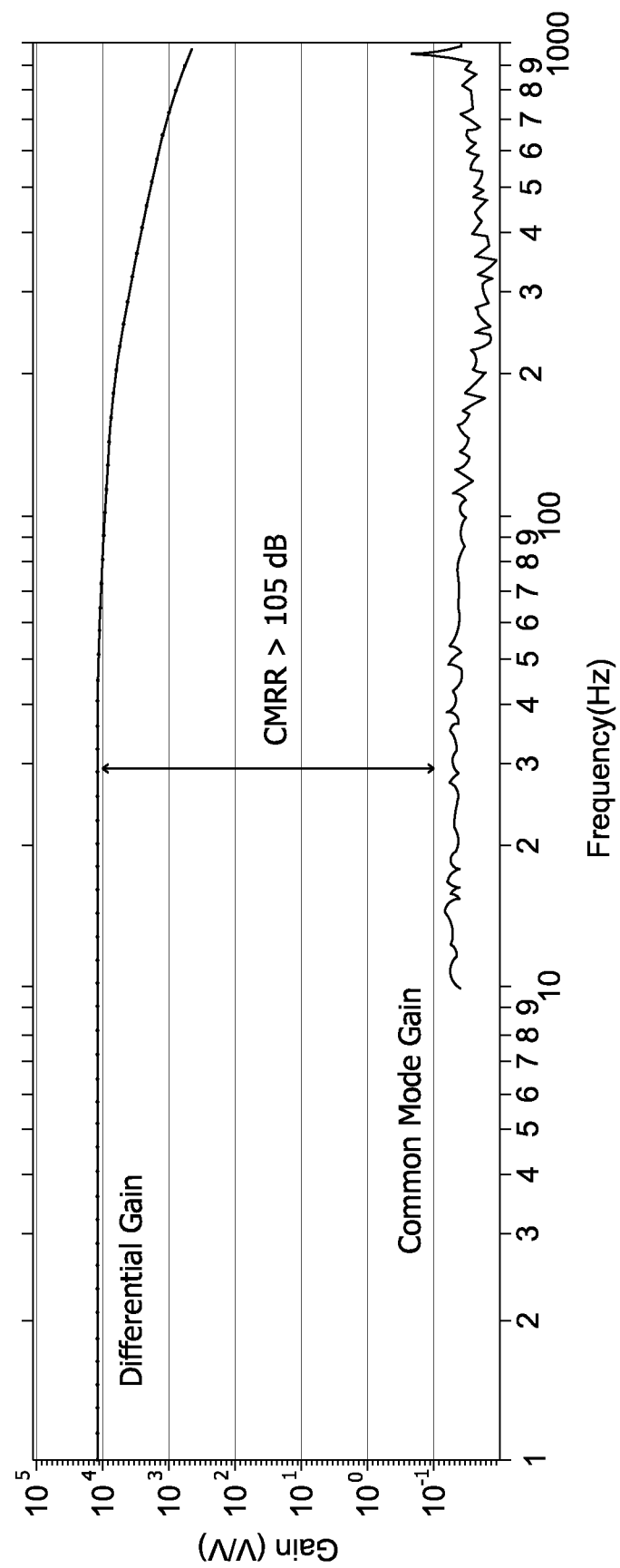
FIG. 12 illustrates common-mode rejection ratio (CMRR) measurement of the IA of FIG. 6.

FIG. 12 shows the CMRR measurement using a 600 mVpp common mode input signal, which corresponds to a CMRR larger than 105 dB in the measurement bandwidth. The differential input impedance of the IA is defined by the off-chip high-pass filter, which is 10 MΩ. From the measured noise density of 85 nV/√Hz, the noise-efficiency-factor (NEF) of the IA can be calculated as 5.0 while using a single TI input stage and a single TC output stage. NEF is described in "A Micropower Low-Noise Monolithic Instrumentation Amplifier for Medical Purposes" by M S J Steyaert, W M C Sansen and C Zhongyuan, IEEE J. Solid-State Circuits, vol. sc-22, no. 6, lines 1163 to 1168, December 1987, which is incorporated herein by reference. As the number of output stages increases, the equivalent NEF of the IA reduces to 4.0 and 3.6 for two and three output stages respectively.

A fundamental requirement for an ECG monitoring system is the detection of the ECG beat (QRS Complex). This is performed by extracting the features of the QRS complex, which is used as an input to a beat detection algorithm. A high performance but rather power hungry feature extraction method is the Continuous Wavelet Transform (CWT) as described in "Low-Power Robust Beat Detection in Ambulatory Cardiac Monitoring" by I Romero, B Grundlehner, J Penders, J Huisken and Y H Yassin, IEEE BioCAS, pages 249 to 252, November 2009, which is incorporated herein by reference.

Figure 13:
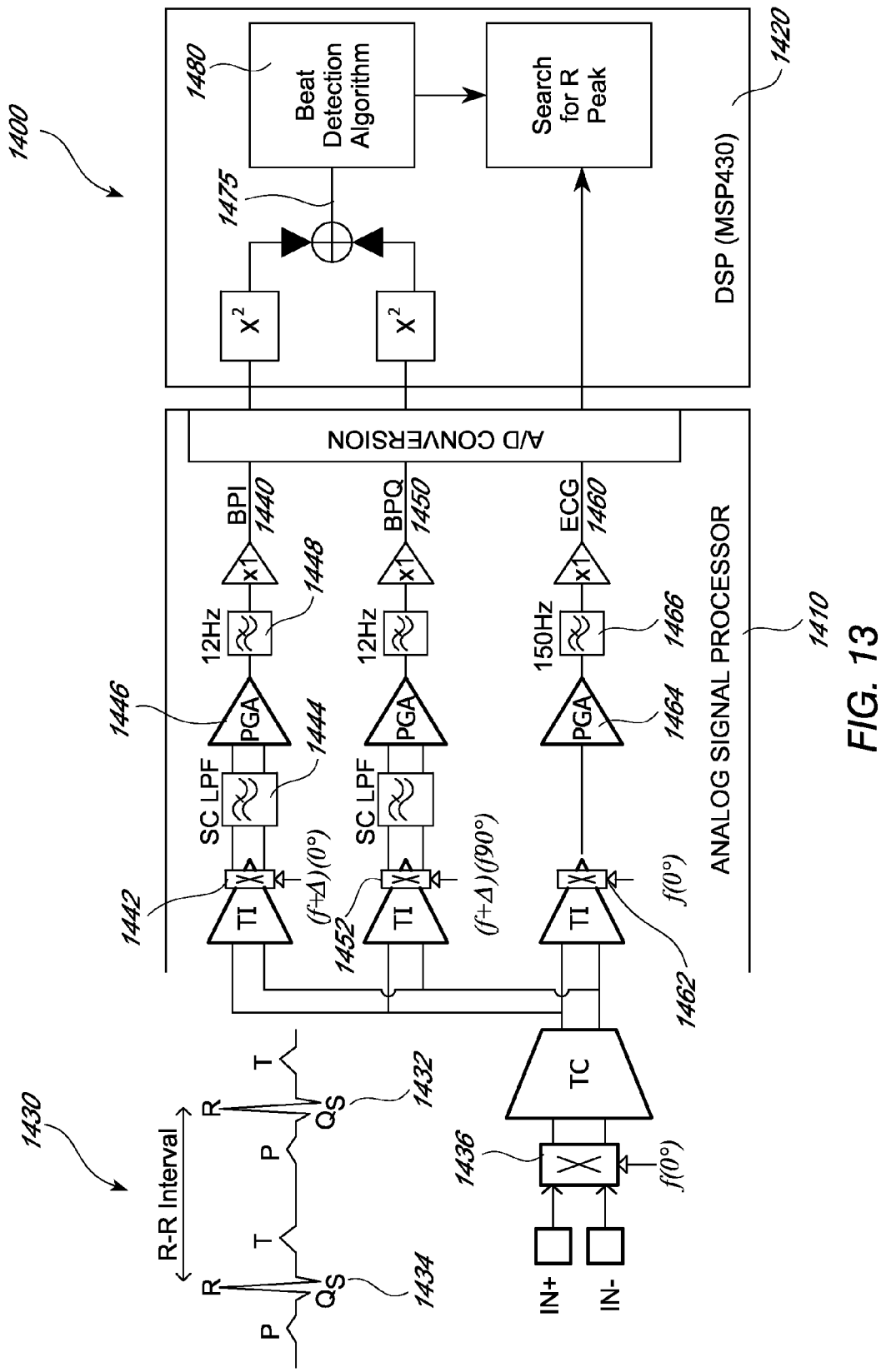
FIG. 13 illustrates an architecture of a low power R-peak detection system.

The power consumption can be lowered by implementing the wavelet filters in the analog domain, while limiting the configurability to different scales. In accordance with one embodiment, a different approach is used that simply uses a band-pass filter to extract the features of the ECG signal. The band-pass filter characteristics are optimized over the MIT-BIH Arrhythmia Database (www.physionet.org/physiobank/database/mitdb) and the use of the heterodyne chopper readout is selected as a power efficient and configurable implementation of a band-pass filter (a band-pass filter known in the art). FIG. 13 shows the architecture of a complete beat detection system 1400 utilizing the heterodyne chopping readout circuit in the ASP 400 (FIG. 3) for extracting the band-power for detecting the QRS complex and referring to the ECG readout channel 410 (FIG. 3) for detecting the location of the R-peak. The beat detection system 1400 comprises an ASP 1410 connected to a DSP 1420. The ASP 1410 receives an input signal 1430 which it processes to extract quadrature components 1440, 1450 of the ECG signal fluctuations in the selected frequency band (corresponding to band power channels 420 in FIG. 3) and extracts a time domain ECG signal 1460 (corresponding to ECG channel 410 in FIG. 3). The extracted components 1440, 1450 and the ECG signal 1460 are digitized by an ADC 1470 (corresponding to AS-ADC 440 in FIG. 3). The digitized components and signals are passed to the DSP 1420 for further processing.

From the digitized quadrature components, the DSP calculates the band-power by taking the sum-of-squares of the quadrature channels 1440, 1450. This band-power is used as an input 1475 to a beat detection algorithm 1480. The beat detection algorithm 1480 detects the presence of the QRS complex 1432, 1434 in input signal 1430 and refers to the digitized time-domain ECG signal 1460 to find the exact location of the R peak within the input signal 1430.

As shown in FIG. 13, a single TC input stage is used for the implementation of the three readout channels for beat detection. Such an architecture reduces the required current consumption of the implemented IA from 4.2 µA (two fully differential IA plus a single-ended IA) to 2.2 µA (a single TC input stage with 2 fully differential and 1 single-ended TI output stages).

The ECG signals measured from electrodes (IN+, IN−) are modulated at the input to the ASP 1410 with an in-phase clock, f(0°), 1436. In this particular implementation, the in-phase clock 1436 operates at a frequency of 1 kHz. Then, the modulated ECG signal is demodulated with a frequency offset (Δ) at the output of two TI stages 1442 and 1452, where (Δ) defines the center of the band-pass filter. The quadrature demodulation clocks enable the extraction of the imaginary and real components. The width of the band-pass filter is defined by the switched capacitor (SC) low-pass filter (LPF) 1444 positioned after the demodulators 1442, 1452. The filtered components are then amplified by PGA 1446 and filtered again by filter 1448. It will be appreciated that although only the band-power I channel has been labeled, identical components can also be used in the band-power Q channel.

Figure 14:
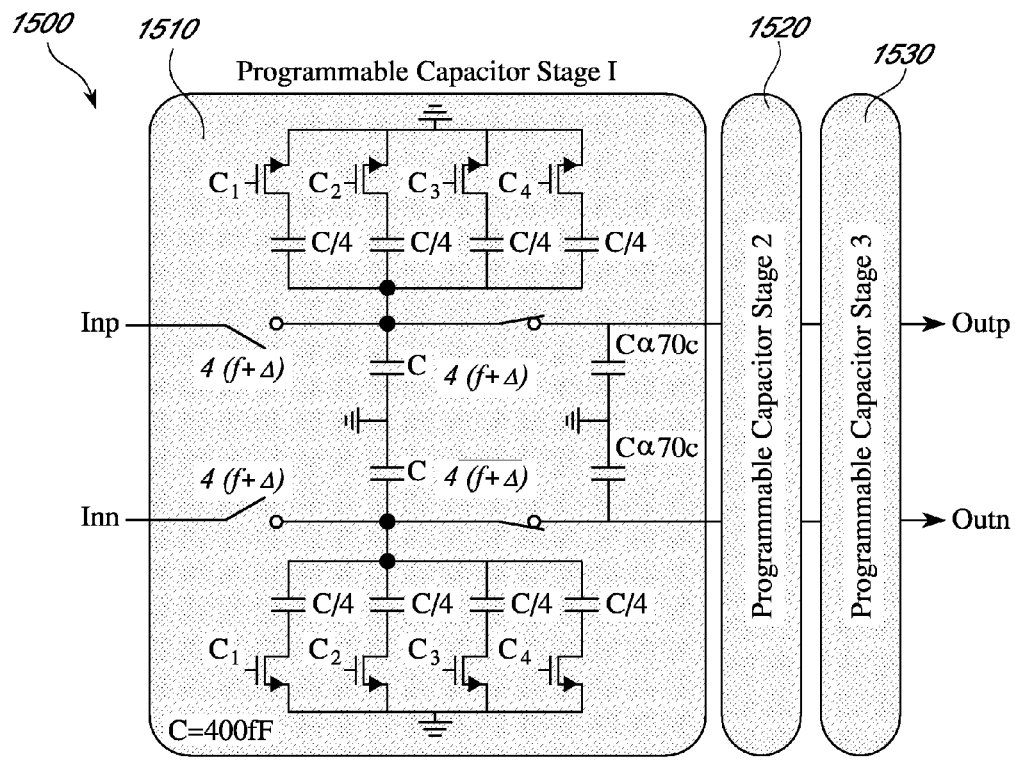
FIG. 14 illustrates a more detailed view of a switched capacitor low-pass filter used in the architecture of FIG. 13.

FIG. 14 shows a switched capacitor (SC) low-pass filter (LPF) 1500 that is used for filtering the quadrature components 1440, 1450 of FIG. 13 in more detail. The SC LPF 1500 provides a good trade-off between area and noise performance. In order to reduce the noise, the SC LPF is operated at four times the chopper demodulation frequency, that is, 4(f+Δ). As shown, the SC LPF 1500 comprises three cascaded programmable capacitor stages 1510, 1520, 1530—only stage 1510 being shown in detail. Each capacitor stage 1510, 1520, 1530 comprises an SC RC filter. The cut-off frequency of a single stage can be expressed by:—

$$f_P = \frac{1}{2\pi RC} = \frac{4(f+\Delta)C_R}{2\pi C_L} \qquad (6)$$

where $C_L$ is the total load capacitance
and $C_R$ is the capacitance implementing the equivalent SC resistor $C_R$ can be changed from C to 2C (where C=400 fF) with four equivalent steps using the control bits $C_n$, changing the pole ($f_p$) of a single LPF stage from 9.45 Hz to 18.9 Hz. Cascading three stages of LPFs results in a three-pole LPF where the poles can be expressed as:

$f_1 = 0.198 f_p$ $f_2 = 1.555 f_p$ $f_3 = 3.2474 f_p$

This sets the −3 dB bandwidth of the complete SC LPF 1500 between 1.87 Hz and 3.94 Hz with two-bit configurability.

Returning to FIG. 13, after amplification in PGA 1446, another SC LPF 1448 having a cut-off frequency of 12 Hz rejects the modulated noise of the PGA 1446.

Figure 15:
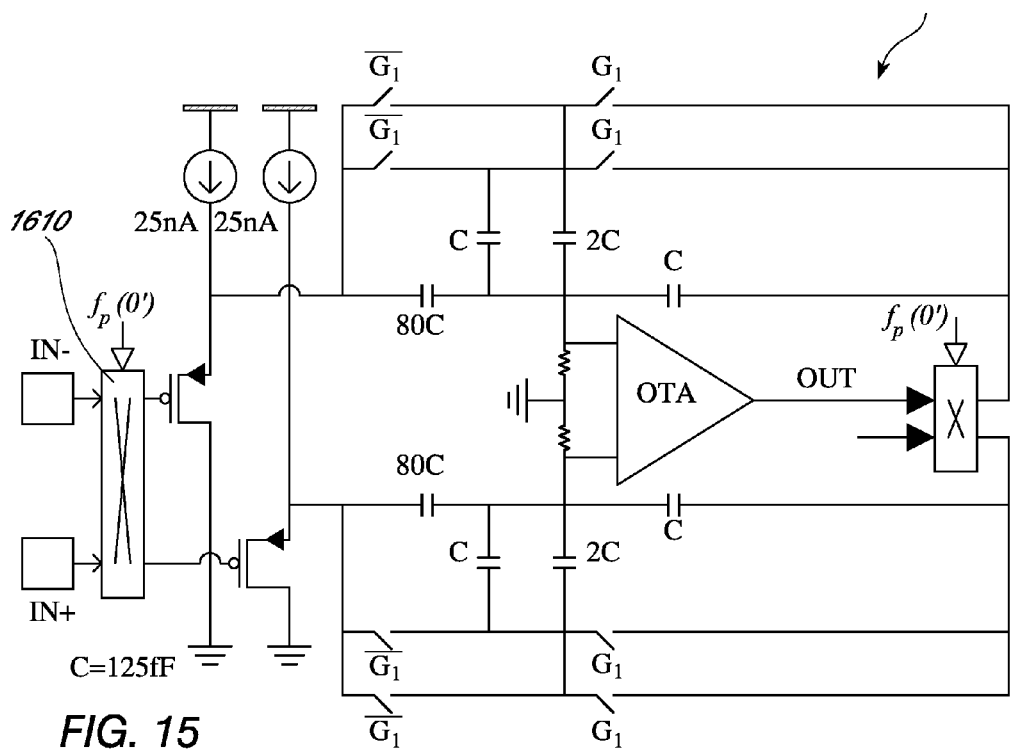
FIG. 15 illustrates a more detailed view of a programmable gain amplifier (PGA) used in the architecture of FIG. 13.

FIG. 15 shows a programmable gain amplifier (PGA) 1600 that is used for amplifying the quadrature components 1440, 1450 of FIG. 13 in more detail. The PGA 1600 of the band-power extraction channel (420 in FIG. 3) is implemented using a chopper modulated capacitive amplifier with three electronically selectable gains of 20, 41 and 83. Due to the large source impedance from the SC LPF 1500 (FIG. 14), the inputs of the PGA 1600 are buffered after input modulator 1610. The modulation frequency is kept relatively low, for example, at 128 Hz, to minimize the loading of the SC LPF 1500 (FIG. 14). The gain of the PGA 1600 is controlled by the positions of the switches G1 and G2. Three gain settings are available with this embodiment as follows:—

| $G_1$ | $G_2$ | GAIN |
|---|---|---|
| 0 | 0 | 83 |
| 0 | 1 | 41 |
| 1 | 1 | 20 |

The implementation of the ECG readout channel in FIG. 13 employs the same input TC stage of the band-power extraction channels. The output stage uses the single-ended TI stage 1462 as shown. The back-end PGA 1464 is implemented using a capacitive amplifier. The gain programmability is integrated using a flip-over architecture. The PGA has electronically settable gains of 3, 5, 9, and 13, setting the gain of the ECG channel to 300, 500, 900, and 1300 respectively. The DC gain of the PGA is 1.

The heterodyne chopper readout uses 1 kHz as the modulation frequency. The required offset frequency (Δ=16 Hz) and the band pass filter width are selected according to a model of the quadrature readout circuit implemented in MATLAB (simulation) together with the rest of the beat detection algorithm 1480. The optimization is done such that the beat detection algorithm 1480 gives the best sensitivity (98.8%) and positive predictability (99.8%) over the MIT-BIH Arrhythmia Database mentioned above.

Figure 17:
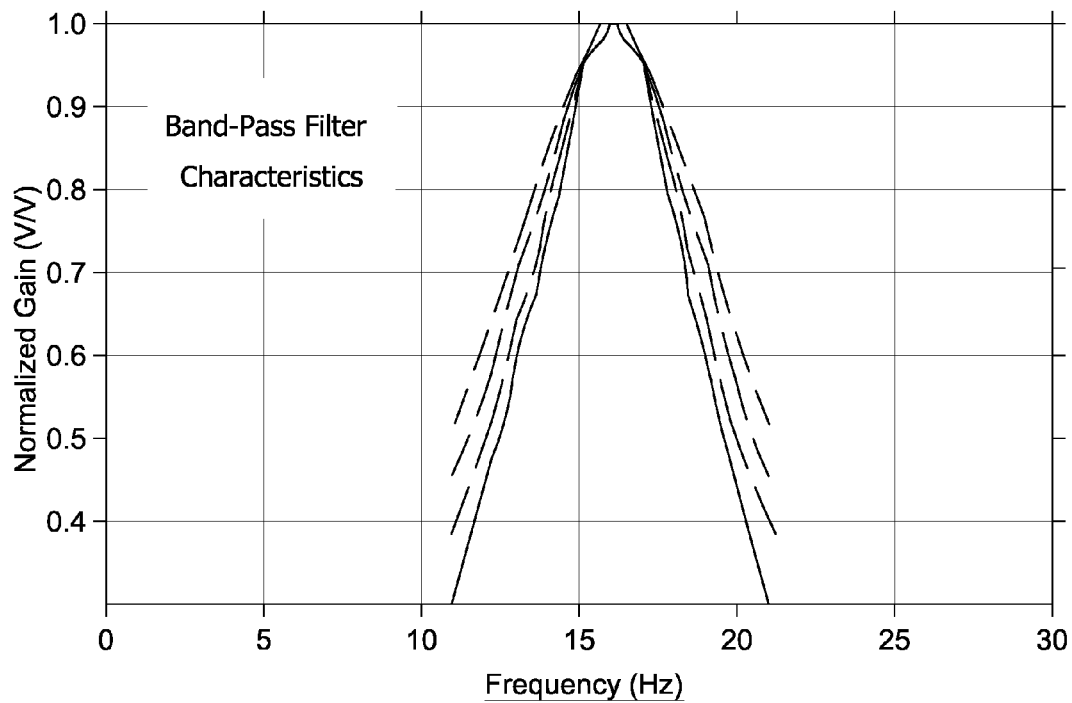
FIG. 17 illustrates band-pass filter characteristics for the measurements that can be used in a band-power extraction circuit.

FIG. 17 shows the measured band-pass filter characteristics of the heterodyne chopper readout circuit. The offset frequency (Δ) is set to 16 Hz using the internal low-frequency oscillators of the ASIC 400 (FIG. 3), whereas the width of the band can be set from twice 2.3 Hz to twice 3.9 Hz with four steps. The low-range of the settings has an offset from the ideal 1.8 Hz value, possibly due to the effect of the parasitic capacitance. The solid line indicates the characteristics used in the measurements.

Figure 18:
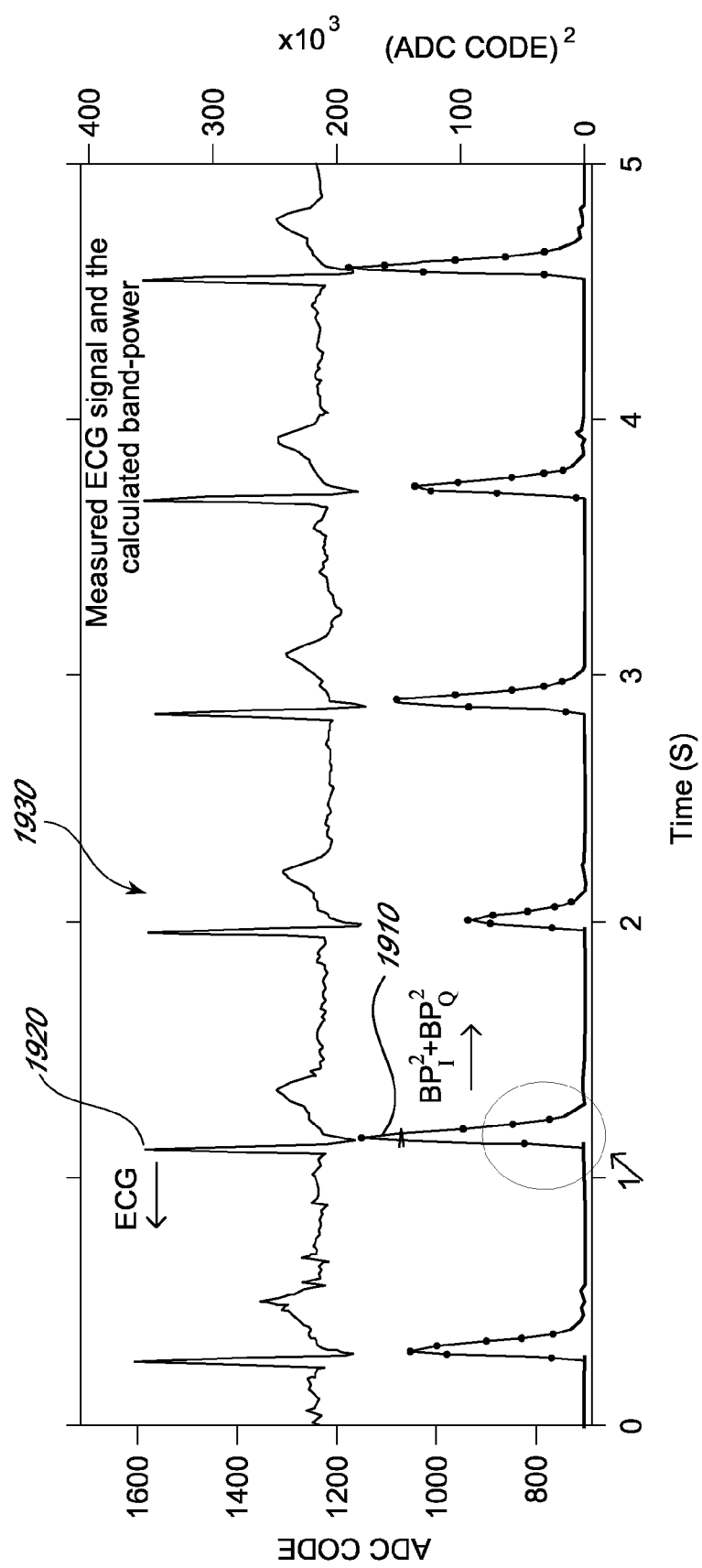
FIG. 18 illustrates a graph of measurements obtained from the band-power extraction circuit of FIG. 3.

FIG. 18 shows the extraction of the band-power in a real ECG recording application using the minimum bandwidth setting of the filter. Upper trace 1904 shows the extracted ECG signal and lower trace 1906 shows the calculated band-power using the band-power quadrature components provided by the ASIC 400 in FIG. 3.

The calculation of the band-power shows clear peaks 1910 during the presence of the QRS complex 1920 in an ECG signal 1930. It should be noted that heterodyne chopping amplifiers folds the odd harmonics of the offset frequency (Δ) as described in "A 5 μW/Channel Spectral Analysis IC for Chronic Bidirectional Brain-Machine Interfaces" mentioned above, into the measurement band with $1/n^2$ scaling. Although this has minor significance for QRS detection, which has the highest frequency components in the ECG signal, it may present a problem, if heterodyne chopping is intended to be used for monitoring P or T waves, in the presence of large QRS complex signal.

Figure 19:
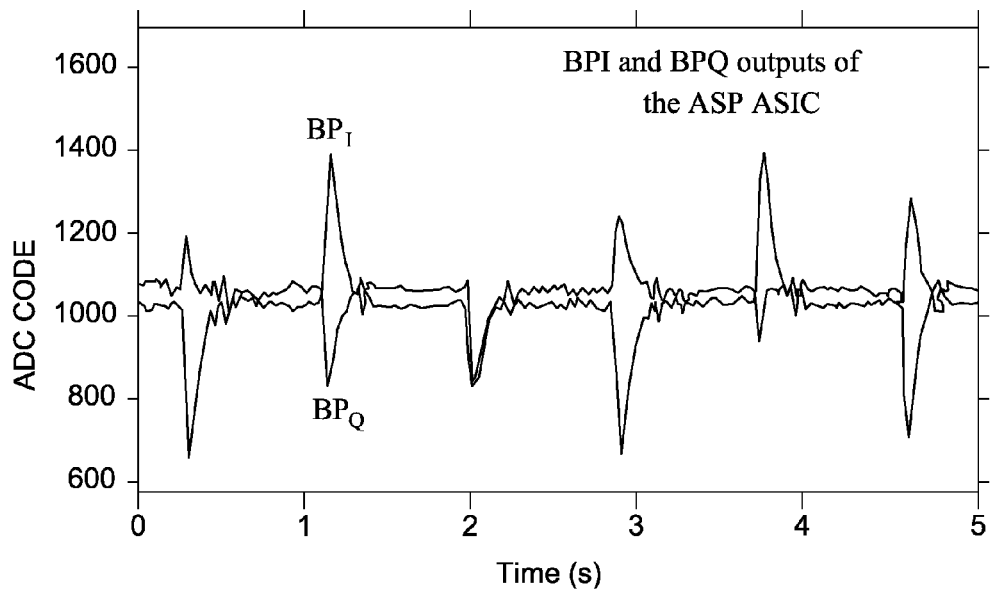
FIG. 19 illustrates an enlarged view of a portion of the graph shown in FIG. 18.

FIG. 19 shows an enlarged view of the power peak 1910 of FIG. 18. The power characteristics for the I and Q components can be seen.

Commonly, portable biopotential monitoring systems follow two approaches, namely, the signals are processed in the system and results are transmitted, or the signals are continuously streamed and the processing takes place at the receiver side. The former type of system can make use of data compression to reduce digital signal processing work load, where as the latter can benefit from it by transmitting significantly less data. Hence, in both approaches, the data compression can lead to significant reduction in the power consumption.

Figure 20:
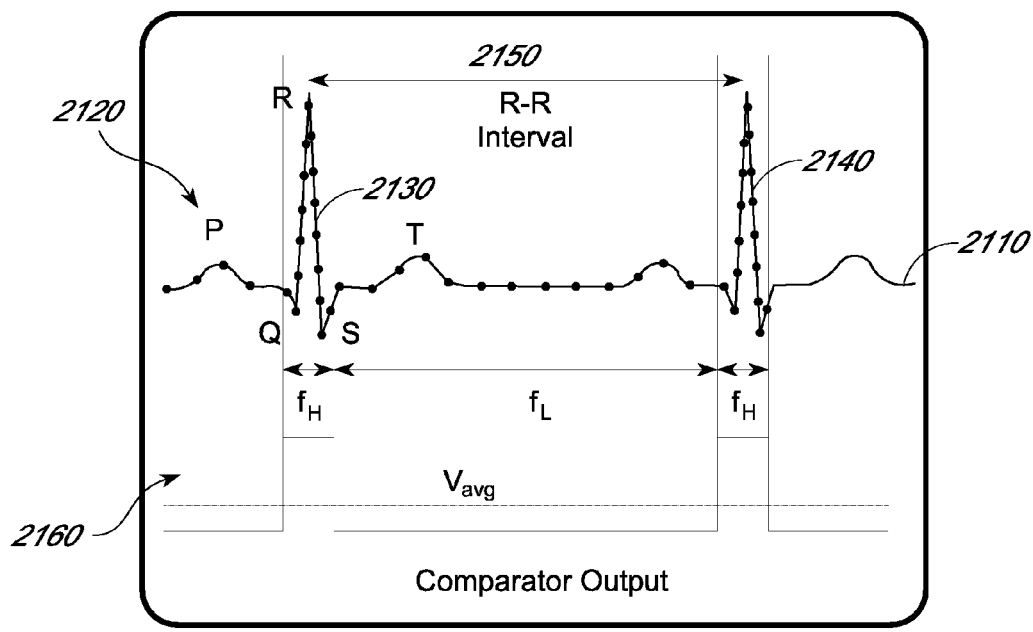
FIG. 20 illustrates the principle of adaptive sampling.

The sampling rate of ECG signals is conventionally selected according to the high frequency region, that is, the QRS complex, and the requirements of the application. For example, heart rate variability (HRV) analysis requires time resolution of the R point in QRS complex. This can benefit from higher sampling rates than the commonly accepted 256 Hz sampling rate of portable ECG monitoring devices. However, such constant sampling rate over the entire ECG signal significantly increases the processing load of systems. Significant data compression without loss of information can be achieved if the sampling frequency of the ECG signals can be adapted according to the activity of the signal as illustrated in FIG. 20. Time samples of an ECG signal 2110 are illustrated by dots in upper trace 2120. In trace 2120, two QRS complex portions 2130, 2140 are shown with an R-R interval 2150. Lower trace 2160 illustrates the comparator output where a high frequency, $f_H$, is selected for the QRS complex 2130, 2140 and a lower frequency, $f_L$, is used for the period between the S of complex 2130 and the Q of complex 2140.

An adaptive sampling ADC (AS-ADC) architecture has been devised that can be used with standard digital signal processing platforms.

Figure 21:
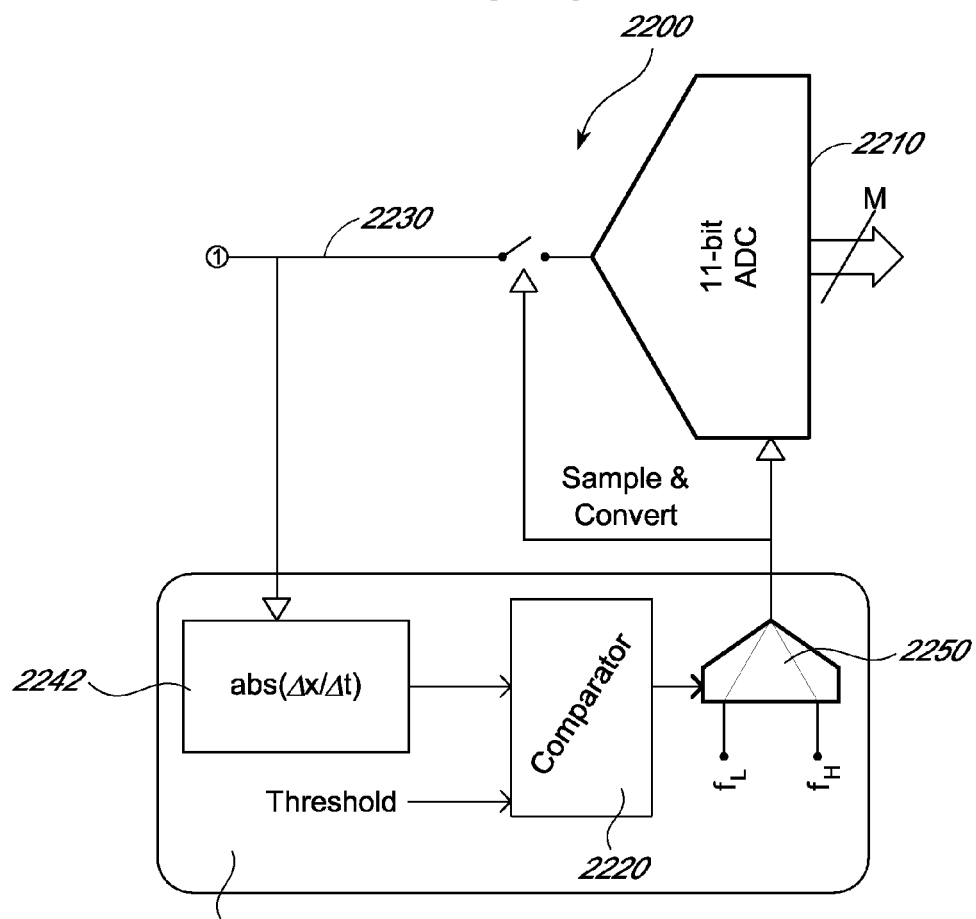
FIG. 21 illustrates a block diagram of the sampling control for adaptive sampling.
Figure 22:
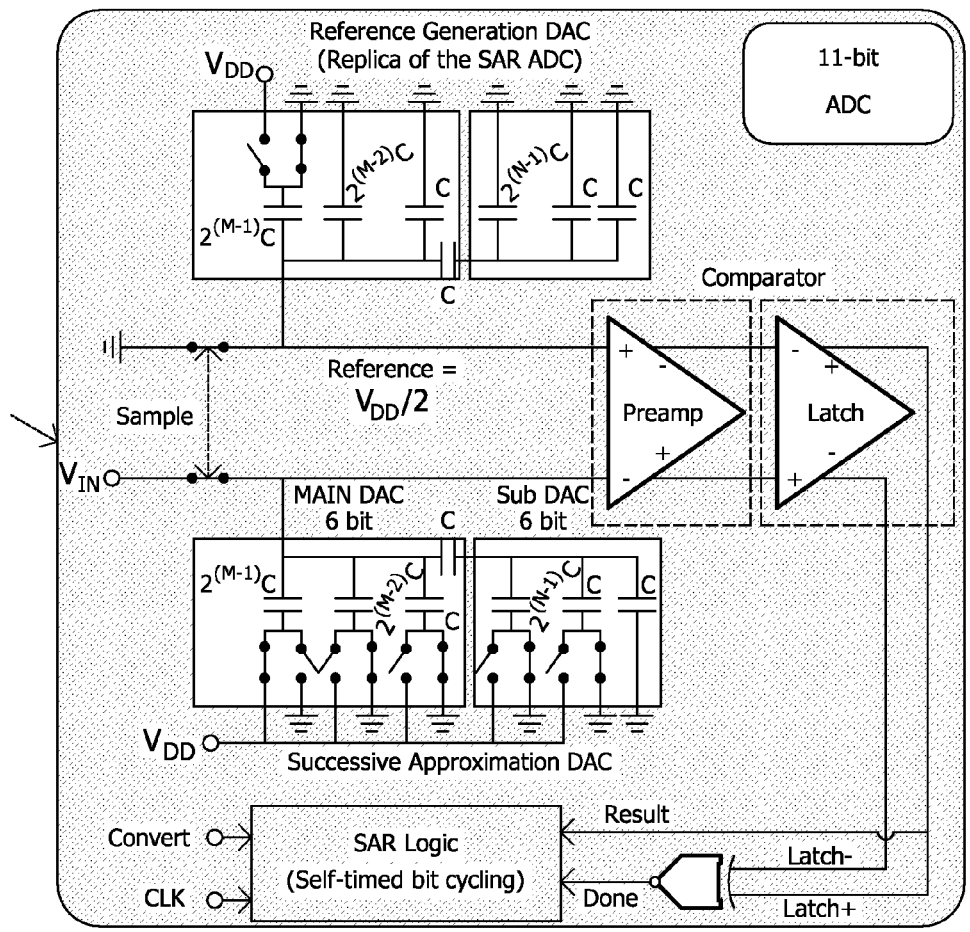
FIG. 22 illustrates the ADC shown in FIG. 21 in more detail.

FIG. 21 shows the architecture of an AS-ADC 2200. An ADC 2210 is core to the architecture and comprises an 11-bit Successive Approximation ADC (SAR-ADC) using split-DAC (as shown in FIG. 22) to reduce the silicon and self-timed bit cycling for relaxing the settling time of a comparator 2220.

In order to enable rail-to-rail input range, the level shifter sampling approach has been used as known in the art. The unit capacitance of the DAC is 400 fF yielding 11-bit resolution in DAC voltage steps across ±3σ mismatches.

The adaptive sampling of an input signal 2230 is controlled by an Activity Detector (ACTDET) circuit 2240 that senses the rate of change of the input signal by using a differentiator 2242. The output of the differentiator 2242 is compared to a threshold voltage in comparator 2220 to select between a low sampling rate, $f_L$, and a high sampling rate, $f_H$, in a selector 2250. The low and high sampling rates in this embodiment are respectively 64 Hz and 1024 Hz. The selection of 1024 Hz sampling rate for $f_H$ increases the time resolution of the time resolution of R peak, whereas 64 Hz is sufficiently large with respect to the frequency content of P and T.

The threshold voltage can be an adaptive threshold that is determined from the heart rate being monitored as described below with reference to FIG. 31.

An important consideration is the delay between the detection of the high frequency activity and changing of the ADC sampling rate. The differentiator 2242 uses switched capacitor (SC) topology where the clock frequency is selected as 250 Hz and two differentiators operating in alternating clock phases are connected in parallel.

Simulations indicate a maximum group delay of 2.5 ms at the output of the differentiator 2242, setting the delay between the detection of the high frequency activity and changing of the ADC sampling rate to this value. This delay is considered not to be significant as most portable recording systems rely on 256 Hz constant sampling rate setting the time accuracy of the same transition region to ~4 ms.

Another important issue is the selection of the threshold voltage. The amplitude and morphology of ECG signals varies significantly, leading to variations in the rate of change information. This necessitates the use of an adaptive threshold. The adaptive threshold generation relies on the periodic nature of the ECG signals as shown in FIG. 20.

The function of the ACTDET 2240 is to detect the high frequency activity, that is, the presence of the QRS complex, and to control the ADC sampling frequency. This means that the comparator output pulse should have the same duration and period as the QRS complex of the ECG signals. If the duty cycle of the comparator output pulse can be represented by $V_{AVG}$ (shown in the lower trace 2160 of FIG. 20), an ideal value of $V_{AVG}$ can be calculated from the heart rate information extracted using the beat detection algorithm 1480 in FIG. 13 and the morphological definition of the QRS width of between 40 ms and 120 ms.

Figure 23:
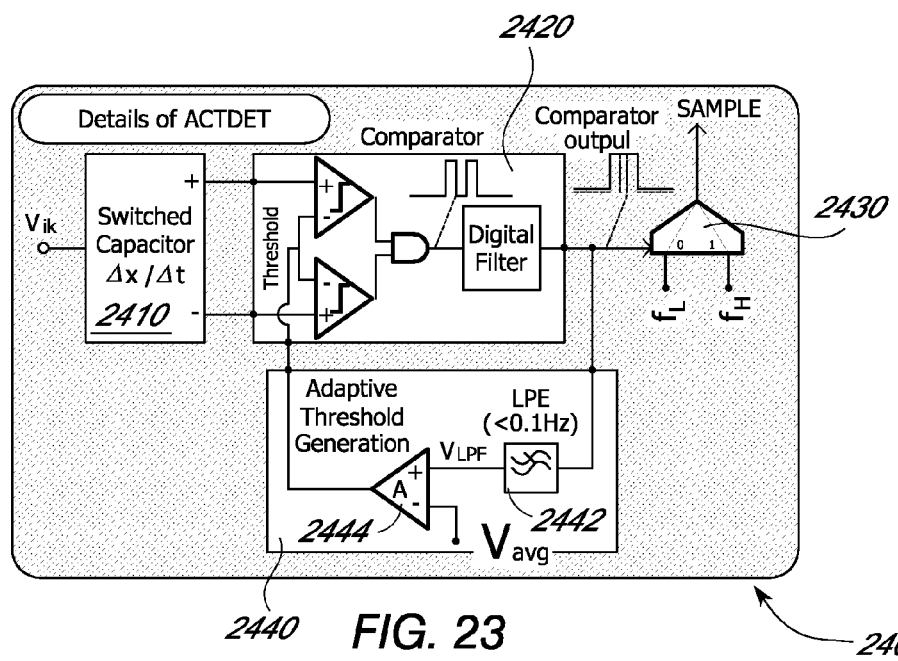
FIG. 23 illustrates the activity detector shown in FIG. 21 in more detail.

In FIG. 23, a detailed implementation of the ACTDET circuit 2240 of FIG. 21 is shown. The ACTDET 2400 comprises a differentiator stage 2410, a comparator stage 2420, a selector stage 2430 and an adaptive threshold generator stage 2440. The differentiator stage 2410 is as described above with reference to FIG. 21.

The adaptive threshold generator stage 2440 forms part of a negative feedback loop in which the output from the comparator stage 2420 is filtered using a LPF 2442 to provide one input to a comparator 2444, $V_{LPF}$. The comparator 2444 compares $V_{LPF}$ to the calculated $V_{AVG}$ so that the threshold voltage can be regulated to match $V_{LPF}$ to $V_{AVG}$. After settling, so that $V_{LPF}=V_{AVG}$, the threshold of the comparator stage is set to increase the ADC sampling frequency only during the presence of the QRS complex.

The transfer function from the input of the SC differentiator to the output of the low-pass filter can be written as:

$$V_{LPF}(s) = \frac{s_p}{s + (1+A)s_p}[V_{IN}(s)H(s) + AV_{AVG}] \quad (7)$$

where H(s) is the transfer function of the SC differentiator 2410
$s_p$ is the cut-off frequency of the LPF 2442
and A is the gain of the feedback amplifier The LPF can be implemented by an RC filter where the resistor, R, can be implemented using pseudo resistors as known in the art. This enables the implementation of a low-pass filter with very low cut-off frequency, averaging the comparator output over a long period. The use of a large loop gain, for example, where A=10, sets $V_{LPF}$ to $V_{AVG}$ and reduces the effect of the SC differentiator output on the threshold voltage.

Figure 24:
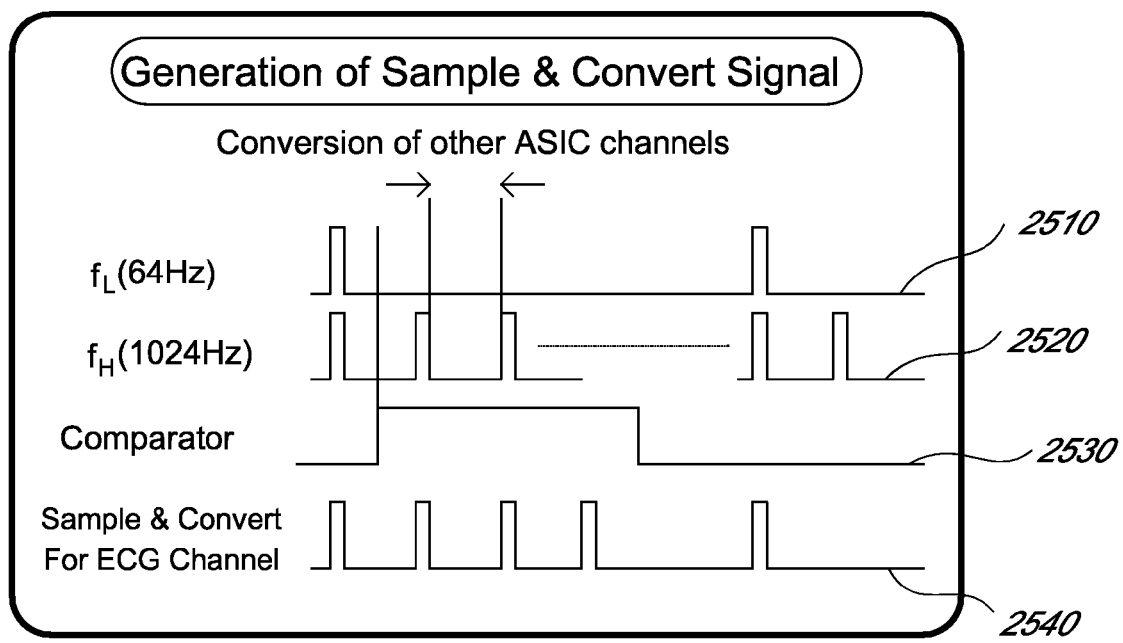
FIG. 24 illustrates the generation of a sample and convert signal for adaptive sampling.

FIG. 24 illustrates the generation of a sample and convert signal for the AS-ADC 2200 of FIG. 21. Trace 2510 shows the low frequency sampling signal, $f_L$, of 64 Hz; trace 2520 shows the high frequency sampling signal, $f_H$, of 1024 Hz; trace 2530 shows the output from the comparator 2220; and trace 2540 shows the sample and convert signals for the ECG channel. In between the high frequency sampling signals, other ASIC channels not requiring the high frequency sampling can be converted.

Figure 25:
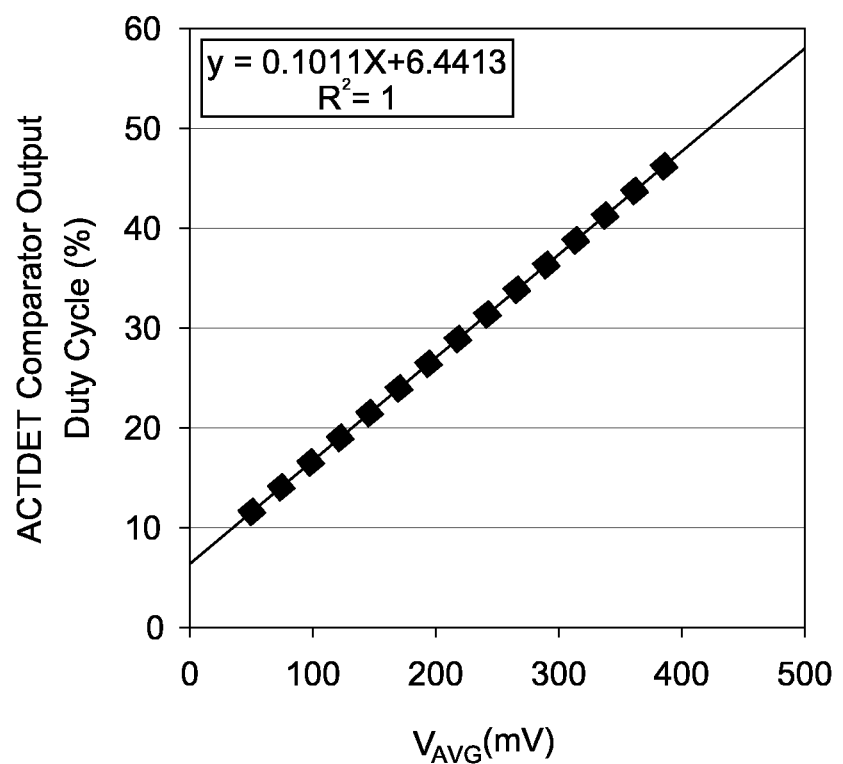
FIG. 25 illustrates a comparator output duty cycle for the activity detector shown in FIGS. 20 and 21.
Figure 26:
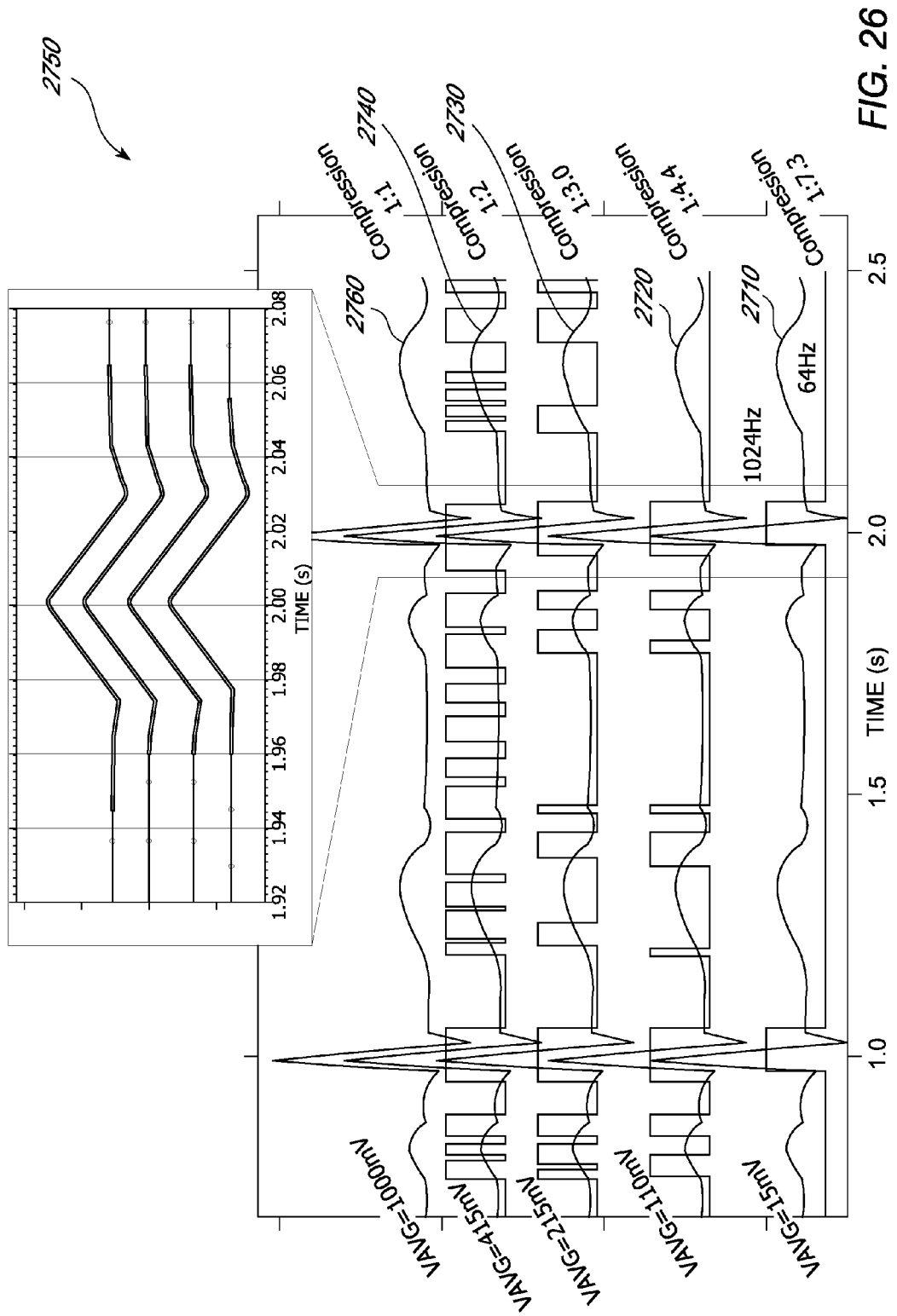
FIG. 26 illustrates the effect of changing $V_{AVG}$ on the output of the ADC shown in FIGS. 20 and 22.
Figure 32:
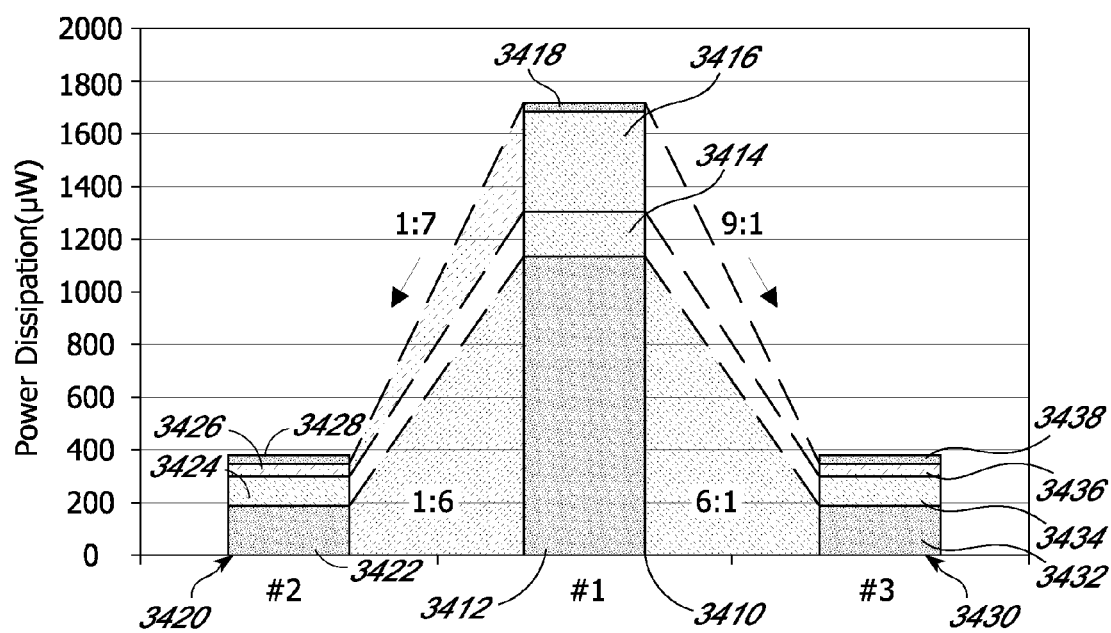
FIG. 32 illustrates a power consumption comparison for different systems utilizing the ASP ASIC in accordance with one embodiment.

In order to characterize the operation of the AS-ADC, a sinusoidal signal is fed to the input of the ADC and the duty cycle of the comparator output pulse is monitored, while changing the $V_{AVG}$ input of the ACTDET block 2240 in FIG. 21. FIG. 25 shows the linear relation between the duty cycle of the comparator output pulse and the input $V_{AVG}$. This enables the setting of the width of the comparator output pulse to the ideal width of the QRS complex once the average beat-to-beat interval is known. FIG. 26 shows the effect of changing the $V_{AVG}$ while sampling a synthetic ECG signal at 60 beats-per-minute. Real life operation is shown in FIG. 32. The ideal value of the comparator output duty cycle is calculated to be between 4% and 12% (QRS complex width is between 40 ms and 120 ms). The average beat-to-beat duration is 1 s. For the first measurement, bottom trace 2710, $V_{AVG}$ is selected as 15 mV causing the ADC to increase the sampling rate from 64 Hz to 1024 Hz only during the presence of the QRS complex. This has a compression ratio of 1:7.3 with respect to a constant 1024 Hz sampling rate. In traces 2720, 2730 and 2740, $V_{AVG}$ is increased to 110 mV, 215 mV, and 415 mV respectively increasing the duty cycle of the high frequency sampling rate, each trace corresponding to compression ratios of 1:4.4, 1:3.0 and 1:2 respectively with respect to a constant 1024 Hz sampling rate. The pulse overlaid on each trace shows the regions sampled with at the high sampling rate of 1024 Hz.

Inset 2750 shows the delay between the start of the QRS complex and switching to the high frequency sampling rate for each of the traces 2710, 2720, 2730 and 2740.

Trace 2760 is also shown in FIG. 26 for a $V_{AVG}$ of 1000 mV and a compression ratio of 1:1 with respect to a constant 1024 Hz sampling rate.

In remote and portable medical signal monitoring applications, a key requirement is to continuously monitor the signal integrity against lead connectivity and motion induced signal artifacts as described in "Minimizing Electrode Motion Artifact by Skin Abrasion" by H Tam and J G Webster, IEEE Trans. on Biomedical Engineering. Vol. BME-24, pages 134 to 139, 1977, which is incorporated herein by reference, where especially the latter significantly reduces the reliability of signal analysis since these artifact signals may have a morphology similar to that of the biopotential signals. A popular approach for removing the motion artifact signals from the biopotential recordings is adaptive filtering which requires the presence of a reference signal that is correlated with the motion artifact signals but uncorrelated with biopotential signals. Among different alternatives as described in the art the use of electrode-tissue contact impedance as the reference signal is particularly attractive since it does not require the use of an additional sensor.

Figure 27:
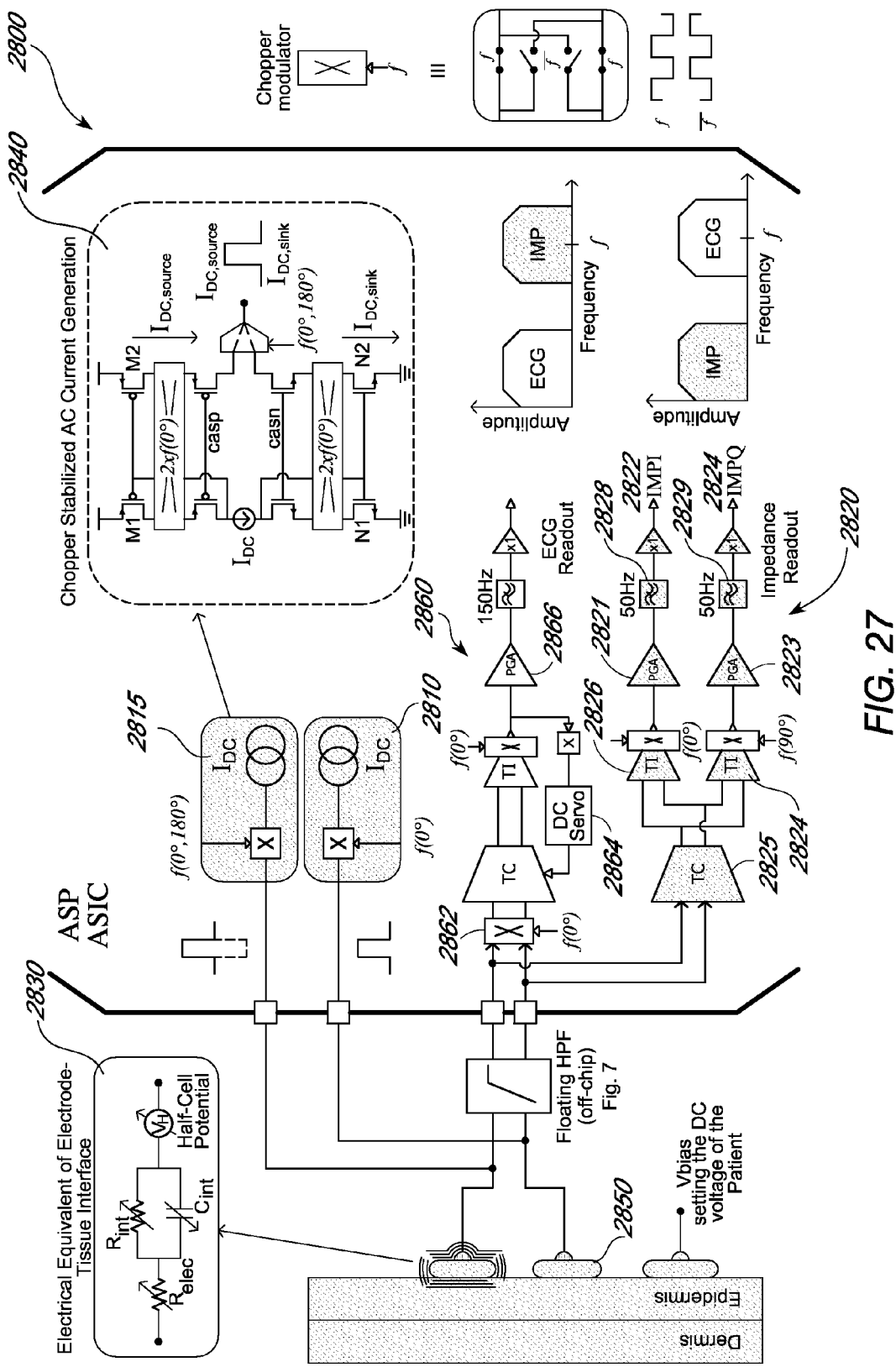
FIG. 27 illustrates an implementation of an electrode-tissue impedance measurement in accordance with one embodiment.

FIG. 27 shows the architecture of the impedance measurement circuit 2800 for continuously monitoring the electrode-tissue contact impedance simultaneously with the biopotential signals. Chopper modulation is used to generate the AC stimulation current and separate the impedance measurement frequency from the biopotential signal frequency.

The impedance measurement circuit 2800 consists of two AC stimulation current sources 2810, 2815 and an impedance readout circuit 2820. The impedance readout circuit 2820 provides two quadrature readout signals 2822, 2824 that correspond to the imaginary and real parts of an electrode-tissue interface 2830. An ECG channel 2830 is also shown.

The AC current sources 2810, 2812 are generated by multiplexing between a current source $I_{DC,source}$, and a current sink $I_{DC,sink}$ at the same frequency, f, as the chopper modulators in the ECG and impedance readout channels 2820, 2830. Chopper stabilized AC current generation is shown in more detail in inset 2840. In order to prevent the generation of the second harmonic, $I_{DC,source}$ should match to $I_{DC,sink}$. This is accomplished by chopper stabilizing the current mirrors $M_1$-$M_2$ and $N_1$-$N_2$ at twice the operating frequency of the chopper modulator, 2f. The phase of a single current source can be selected between 0° and 180°. The former leads to the generation of a common-mode stimulation current that can be used to monitor the impedance difference between two electrodes 2850, 2852 and the latter leads to the generation of a differential stimulation current that can be used to measure the total impedance of the measurement electrodes 2850, 2852. The stimulation current is adjustable between 11 nApp and 100 nApp with 9 steps.

The quadrature impedance readout channel 2820 utilizes a single input TC stage 2825 and two output TI stages 2826, 2827. Similar to the heterodyne readout described above, this minimizes the current consumption of the IA implementation to 1.8 µA for a single TC stage with two output TI stages. The demodulators inside the TI output stages 2826, 2827 are operating at the same frequency as the square wave current sources, that is, at 1 kHz. This way the AC voltage generated over the electrode-tissue interface 2830 can be demodulated to the baseband, whereas the ECG signal at the baseband can be modulated and rejected by a low-pass filter 2828, 2829.

Conversely, ECG readout channel 2860 sustains the impedance voltage at modulation frequency and thus it can be rejected by a low-pass filter. It should be noted that input modulator 2862 of the ECG readout channel 2860 also demodulates the impedance signal to the base-band. In order to prevent the saturation of ECG readout channel 2860 under large electrode impedance mismatches, a DC servo 2864 is included in the ECG readout channel 2860. This DC servo 2864 filters both the offset of the IA, as described in "A 60 µW 60 nV√Hz Readout Front-end for Portable Biopotential Acquisition Systems" mentioned above, and the impedance signal demodulated to the baseband after the input modulator of the ECG readout channel 2860.

Figure 16:
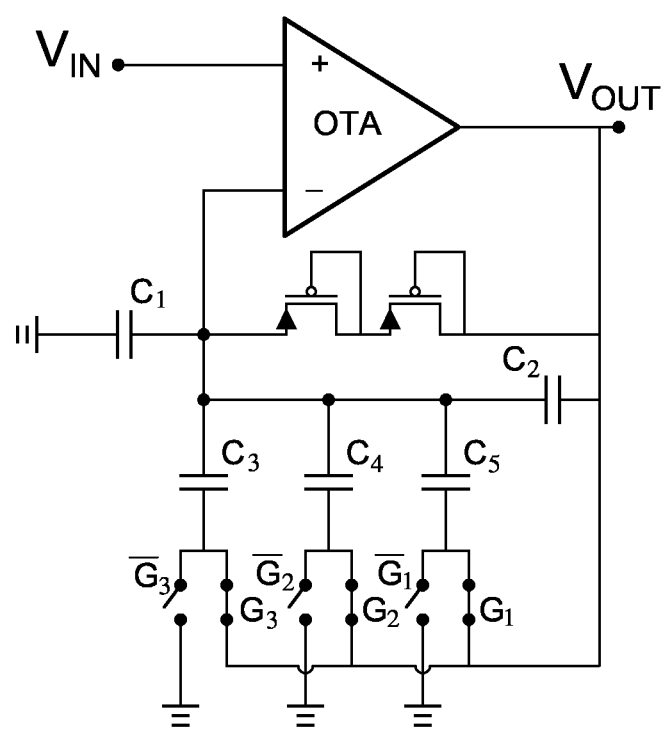
FIG. 16 illustrates an architecture of a PGA of an ECG readout channel described in FIG. 3.

PGAs 2821, 2831 of the impedance readout channel 2820 uses the same architecture as PGA 2866 of the ECG readout channel 2860 as described above with reference to FIG. 16 implementing electronically selectable gains of 3, 5, 9 and 13. The high-pass filtering nature of the PGA with a DC gain of 1 enables the amplification of AC impedance changes while still allowing monitoring of the DC impedance of the electrode-tissue interface. This is crucial for detecting electrode connectivity.

Figure 28:
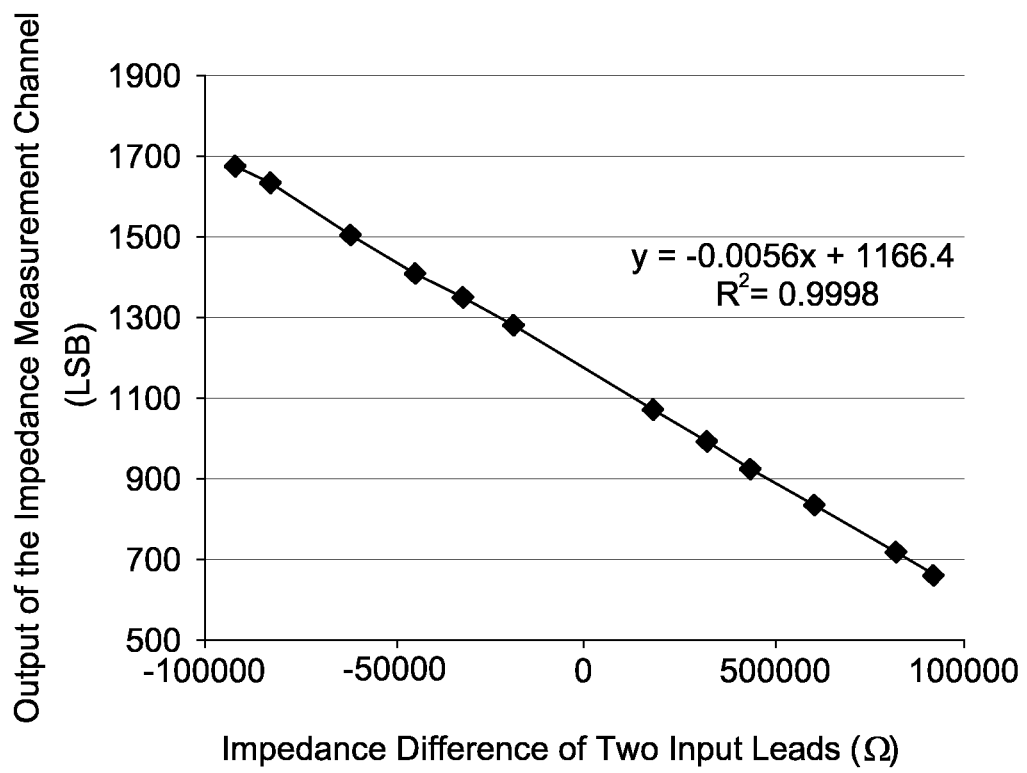
FIG. 28 illustrates a characterization of the impedance measurement shown in FIG. 27.

FIG. 28 shows the characterization of the impedance measurement channel 2820 using off-chip resistors. Two resistors are connected to the input leads of the ASIC 400 (FIG. 3), two AC current stimulation sources are set to 100 nApp with same phase, and the output of the impedance measurement channel (real) is monitored. The output voltage shows a linear change together with the changing impedance of the impedance measurement channel. The fitted curve to the measurements indicates that the stimulation current for the measurement of the impedance is 56 nA, close to the desired value of 50 nA. Note that the total gain at the output of the channel is 100 since PGA gain is 1 for DC inputs. Using the noise measurement of the IA, the equivalent sensitivity of the impedance measurement channel is calculated as 1.7 $\Omega_{rms}/\sqrt{Hz}$ for 100 nApp stimulation current and 90 $\Omega_{rms}/\sqrt{Hz}$ for 11 nApp stimulation current, while the total power consumed for the quadrature impedance measurement is less than 6.5 µW.

Figure 29:
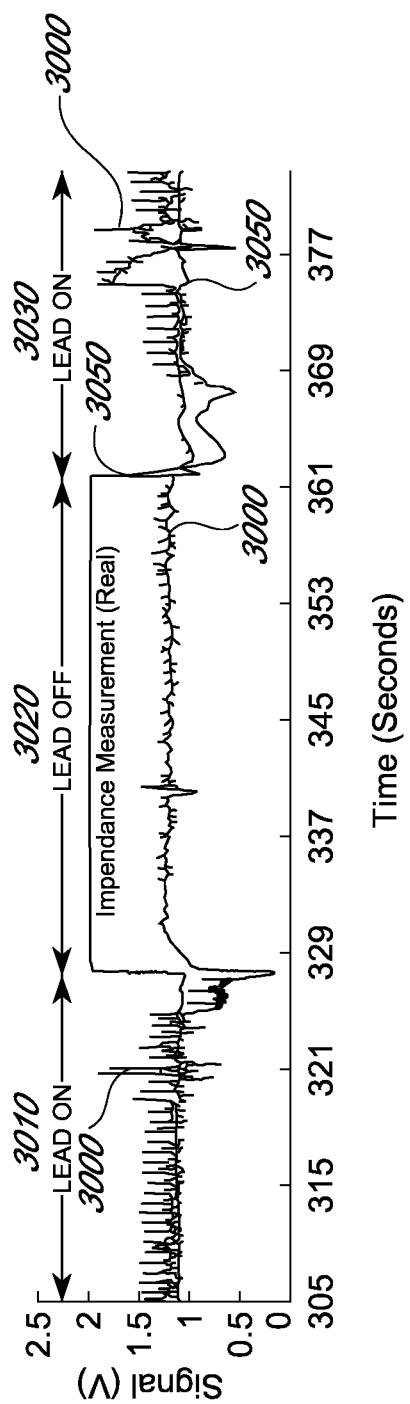
FIG. 29 illustrates the effect of a lead coming off on impedance measurement.

Two other tests were performed under real life conditions on a subject using silver/silver chloride (Ag/AgCl) electrodes without gel to test the usability of the impedance measurement readout for motion artifact monitoring and lead connectivity detection. FIG. 29 shows lead off detection during impedance monitoring and FIG. 30 show motion artifact monitoring through the extraction of electrode-tissue contract resistance and reactance.

In FIG. 29, a monitored ECG signal 3000 is shown together with an impedance measurement for the real component 3050. The two signal traces as shown comprise three regions 3010, 3020 and 3030 where the lead is either connected to the subject or not. Regions 3010 and 3030 show the results when the lead is connected and region 3020 show the results when the lead is no longer connected as it has fallen off. From this, it can be clearly determined when one of the measurement leads is disconnected, as the impedance readout channels give a clear indication of the presence of a disconnected lead.

Figure 30:
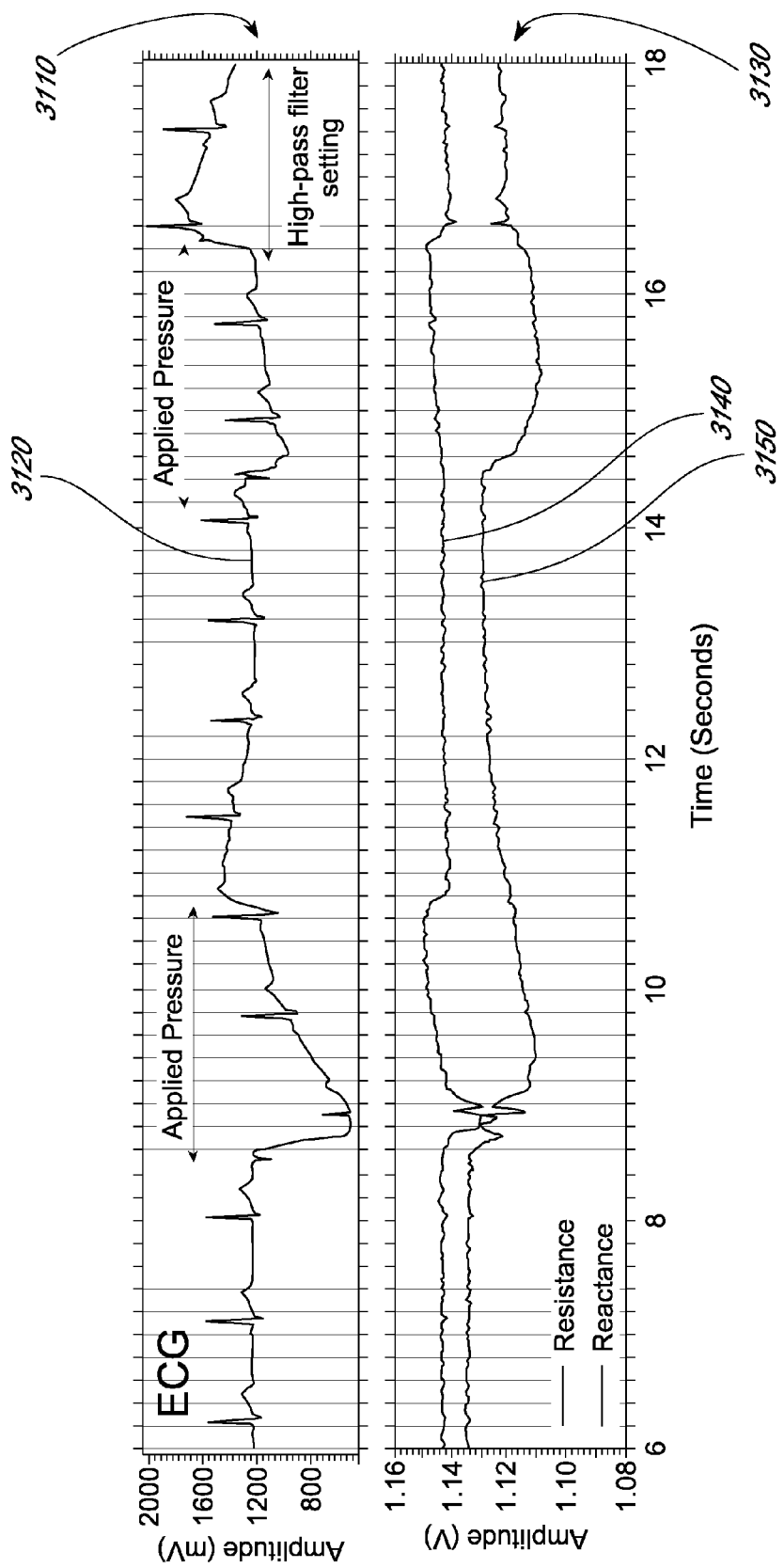
FIG. 30 illustrates the effect of a motion artifact on extracting electrode-tissue contact resistance and reactance.

In FIG. 30, upper trace 3110 shows an ECG signal 3120 and lower trace 3130 shows reactance 3140 and resistance 3150. Here, when a motion related artifact is introduced to the ECG signal 3120 by applying a pressure to one of the recording electrodes, the imaginary and the real components of the impedance readout circuit show an impedance change, indicating the presence of motion artifacts. The measurements were taken with 100 nApp current stimulation where both current sources are in-phase. The gain of the impedance readout channel was 1300.

The ASP ASIC in accordance with one embodiment has been implemented in a 0.5 µm standard CMOS.

The power breakdown of the ASP ASIC indicating the contribution of each building block is shown in Table 3 below.

TABLE 3

| | |
|---|---|
| Analogue Readout Front-End (Total) | 5.3 µA |
| IA Input Stage | 1 µA |
| IA Output Stage - Single-Ended | 400 nA |
| IA Output Stage - Differential | 350 nA |
| DC Servo | 150 nA |
| PGA (Band-Power) | 150 nA |
| PGA (ECG) | 62.5 nA |
| PGA (Impedance Measurement) | 75 nA |
| Band-Gap Reference and Bias Circuit | 2 µA |
| Two Low-Frequency Oscillators | 0.65 µA |
| High-Frequency Oscillator | 0.7 µA |
| ADC Buffer | 0.45 µA |
| Activity Detection Circuit | 0.4 µA |
| Chopper Stabilized AC Current Generation | 0.45 µA |
| ADC and SPI (2 kHz total conversion rate) | 2.2 µA |
| Total Current (Adaptive Sampling OFF) | 15.25 µA |
| Total Current (Adaptive Sampling ON) | 13.25 µA |

When the adaptive sampling is turned on, the ASP ASIC current consumption is reduced by 2 µA mainly due to the reduction in the ADC and SPI current consumption.

Table 4 below shows a summary of the measured performance.

TABLE 4

| | |
|---|---|
| Supply Voltage | 2 V |
| Common-Mode Rejection Ratio with floating HPF | >105 dB |
| Chopper Stabilized Current Source Output | 50 nApeak-5.5 nApeak (9 settings) |
| Input Referred Noise | |
| ECG Channel | 85 nV$_{rms}$/√Hz |
| Impedance Measurement | 1.7 Ω$_{rms}$/√Hz-9 Ω$_{rms}$/√Hz |
| GAIN | |
| ECG Channel | 300, 500, 900, 1300 (4 settings) |
| Impedance Channels | 300, 500, 900, 1300 (4 settings) |
| Band-Power Extraction Channels | 810, 1620, 3240 (3 settings) |
| BANDWIDTH | |
| ECG Channel | 170 Hz, 140 Hz (2 settings) |
| Impedance Channels | 50 Hz |
| Band-Power Extraction Channels | 4.6 Hz, 5.2 Hz, 6 Hz, 6.8 Hz |
| (centre frequency adjustable through LF oscillator) | (−3 dB of BPF) |
| ADC | |
| DNL | 0.3LSB |
| INL | 0.5LSB |
| ENOB | 10.6 bits |

A portable and wireless ECG monitoring system has been developed using the ASP ASIC described above to perform real-time ECG monitoring, beat detection, and signal integrity monitoring. Such a system is shown in FIG. 31.

Figure 31:
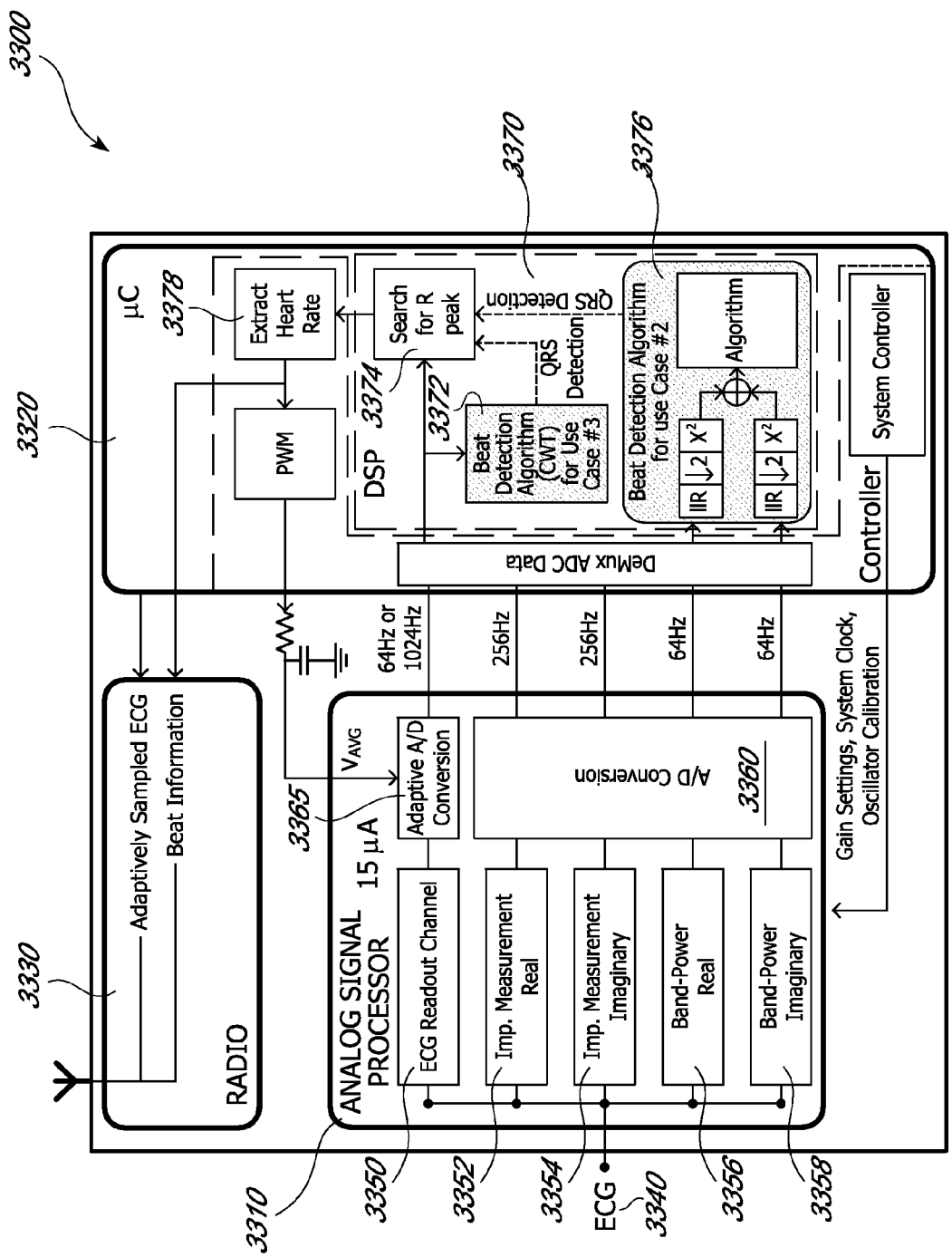
FIG. 31 illustrates an architecture of wireless ECG monitoring using an ASP in accordance with one embodiment.

In FIG. 31, a wireless ECG monitoring system 3300 is shown that comprises an ASP ASIC 3310, a low-power microcontroller (μC) 3320 and a low-power radio 3330.

As shown in FIG. 31, the ASP 3310 receives an input ECG signal 3340 that is processed by an ECG readout channel 3350, impedance measurement channels (real and imaginary) 3352, 3354, and band-power measurement channels (real and imaginary) 3356, 3358. Outputs from the impedance measurement channels 3352, 3354, and band-power measurement channels 3356, 3358 are passed to an ADC 3360 which samples the impedance measurement channels at 256 Hz and the band-power channels at 64 Hz. An adaptive sampling ADC 3365 is used for the ECG readout channel 3310 under the control of a V$_{AVG}$ signal from the μC 3320 at either 64 Hz or 1024 Hz as described above. The digitized signals are passed to a DSP 3370 where they are processed to provide beat detection 3372 and R peak location 3374. QRS detection 3376 is also carried out to provide an input for the R peak location 3374. The output from the R peak location 3374 is used to extract the heart rate 3378 for controlling the adaptive ADC 3365 and for transmission to a receiver (not shown) by means of the radio 3330. The μC 3320 also includes a system controller 3380 that provides control settings, for example, gain settings, system clock and oscillator calibration, for the ASP 3310.

In order to demonstrate the benefits of the ASP ASIC of one embodiment on the system power consumption, different use cases were implemented using the same system. The results are shown in FIG. 32.

In the first scenario, the system does not employ the ASP functionalities of the ASIC but rather only utilizes the ECG readout channel in the ASP ASIC that is sampled at 256 Hz. Raw ECG signals from the ECG readout channel are used for beat detection processing based on a continuous wavelet transform (CWT) and continuous streaming of the ECG signal over the radio or wireless link. The total power dissipation is shown as 3410 with the power dissipation for each of the main components being indicated as 3412 for the radio, 3414 for the controller, 3416 for the DSP and 3418 for the ASP.

In the second scenario, the system employs the ASP functionalities of the ASIC. The μC calculates the band-power using the outputs of the ASP ASIC, which is used as an input to an algorithm that detects the QRS component of ECG signals. Later, the system refers to the adaptively sampled time-domain ECG signal where $f_L$=64 Hz and $f_H$=1024 Hz to find the exact location of the R-peak within the detected QRS component. The μC calculates the average heart rate using the R-R intervals and updates the V$_{AVG}$ of the AS-ADC. The adaptively sampled ECG signal is time stamped and transmitted over the wireless link together with the beat information. Here, the total power dissipation is shown as 3420 with the power dissipation for each of the main components being indicated as 3422 for the radio, 3424 for the controller, 3426 for the DSP and 3428 for the ASP.

Figure 33:
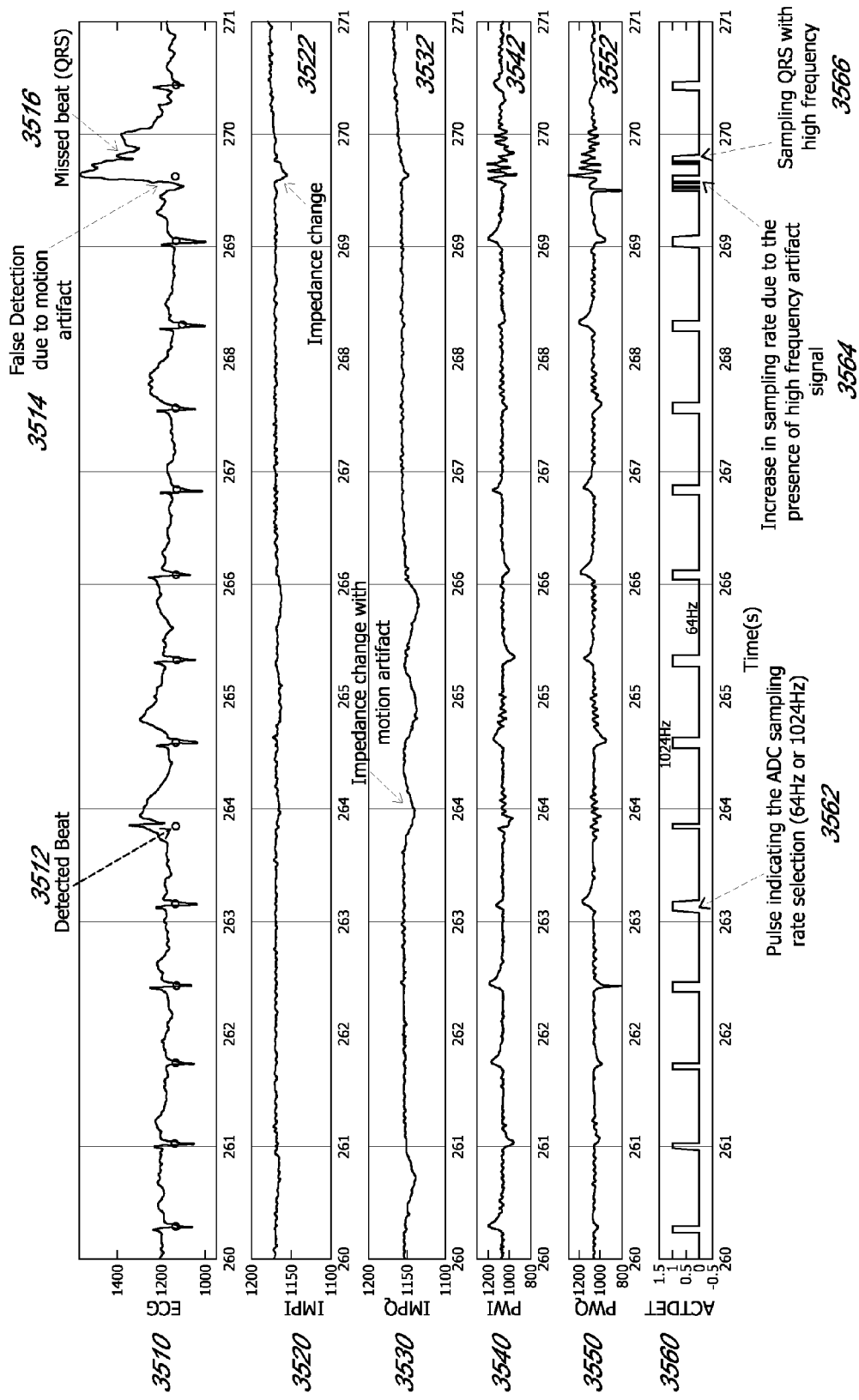
FIG. 33 illustrates measurements taken from a wireless ECG monitoring system using the ASP ASIC in accordance with one embodiment.

The measurement results taken on a subject using the second scenario are shown in FIG. 33.

In the third scenario, which is an alternative to the second scenario, the system employs the adaptively sampled ECG signal where $f_L$=64 Hz and $f_H$=1024 Hz both for beat detection and radio or wireless transmission. In this case, the QRS detection relies on the feature extraction by CWT, which is the equivalent of the algorithm running in scenario #1. Here, the total power dissipation is shown as 3430 with the power dissipation for each of the main components being indicated as 3432 for the radio, 3434 for the controller, 3436 for the DSP and 3438 for the ASP.

Whilst the ASP power dissipation is approximately the same in all three scenarios, it can clearly be seen that there is a substantial reduction in power dissipation between the first scenario and each of the second and third scenarios. In particular, from the first scenario to the second scenario, there is a 7:1 reduction for the DSP and 6:1 reduction for the radio with a small reduction for the controller. Similarly, from the first scenario to the third scenario, there is a 9:1 reduction for the DSP with a 6:1 reduction for the radio, again with a small reduction for the controller.

The μC power consumption is split into the power consumption of the controller and DSP functions. It can be seen from the graph that the use of ASP functionality significantly reduces the DSP and radio power consumption both for the second and third scenarios. For the second scenario, the DSP power dissipation can further be reduced by a factor of 2 by moving the IIR filter in the QRS detection 3376 (FIG. 31) of the DSP to the analogue domain. As the comparison shows, the power consumption of the third scenario is also significantly lower than that of the first, although both systems are running the same QRS detection algorithm.

Turning now to FIG. 33, real life measurements using Ag/AgCl electrodes without any gel were taken. Top trace 3510 shows the ECG signal illustrating a detected beat 3512, false detection 3514 due to motion artifact and a missed beat 3516 in the QRS complex. Traces 3520 and 3530 illustrate the quadrature components (imaginary and real respectively) of the impedance measurement channels. In trace 3520, there is an impedance change at 3522 and, in trace 3530, there is an impedance change at 3532 due to a motion artifact. Traces 3540 and 3550 illustrate the band-power quadrature components (imaginary and real respectively) of the band-power measurement channels. Fluctuations 3542 and 3552 are shown that correspond to the false detection 3514/missed beat 3516 scenario. Bottom trace 3560 illustrates pulses 62 that indicate the selection of sampling at the higher rate, that is, at 1024 Hz. An increase in sampling rate due to the presence of a high frequency artifact is shown at 3564 and sampling QRS with high frequency at 3566.

Various operation phases of an ECG monitoring device including an ASP ASIC in accordance with one embodiment will now be described.

Figure 34:
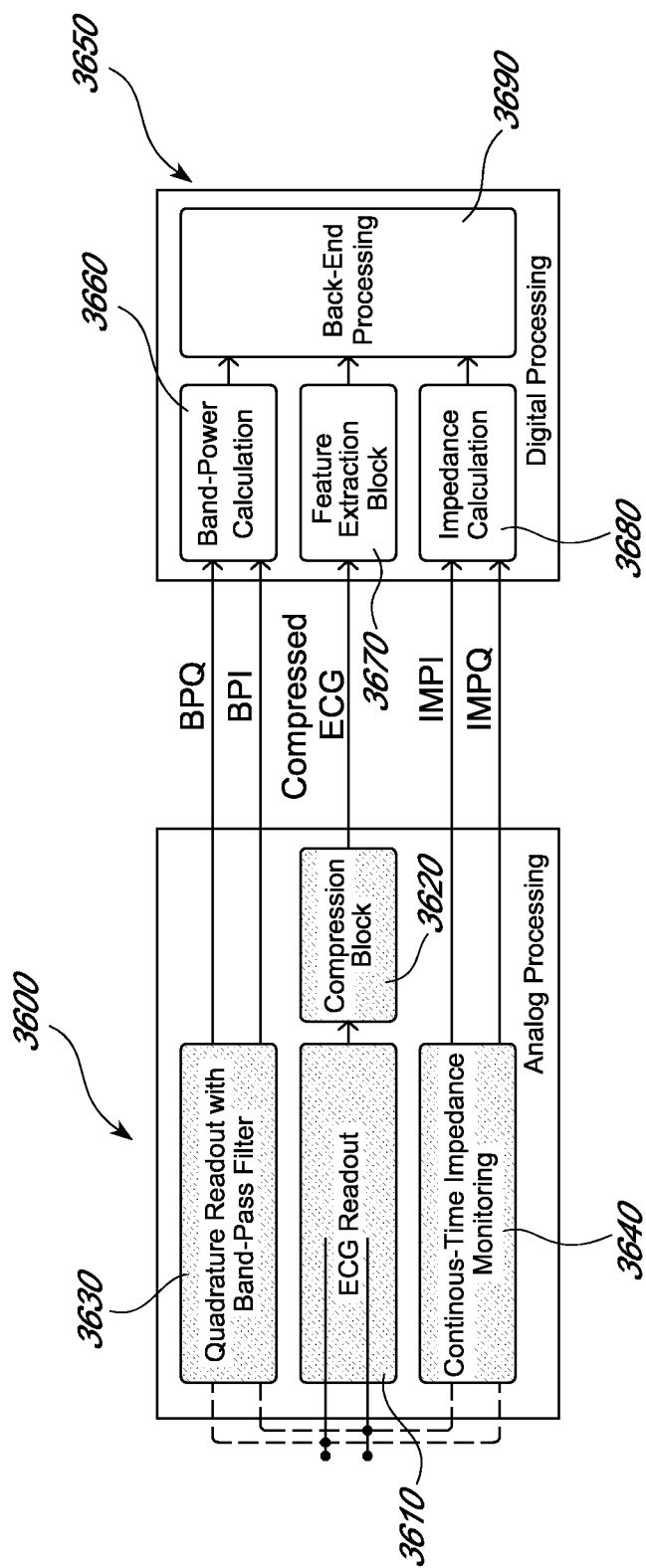
FIG. 34 illustrates a block diagram of an ASP in accordance with one embodiment connected to a digital signal processor.

In FIG. 34, an ASP 3600 in accordance with one embodiment is shown together with a digital processor 3650 to which output signals from the ASP 3600 are connected.

As described above, the ASP 3600 includes an ECG readout channel 3610 connected to an adaptive sampling unit or compression block 3620, a band power readout channel 3630 that provides quadrature output signals BPQ and BPI, and a continuous-time impedance monitoring channel 3640 that provides quadrature output signals IMPI and IMPQ as shown.

The digital signal processor 3650 includes a band-power calculation block or unit 3660, a feature extraction block or unit 3670, an impedance calculation block or unit 3680 and a back-end processor 3690.

The band-power calculation unit 3660 determines the power in the monitored ECG signal as described above and illustrated in FIG. 18 and passes it to the back-end processor 3690. Similarly, the impedance calculation unit 3680 calculates the impedance of the monitored ECG signal and passes it to the back-end processor 3690. The Compressed ECG signal from the compression block 3620 is processed by the feature extraction block 3670 and the output is passed to the back-end processor 3690.

Figure 35:
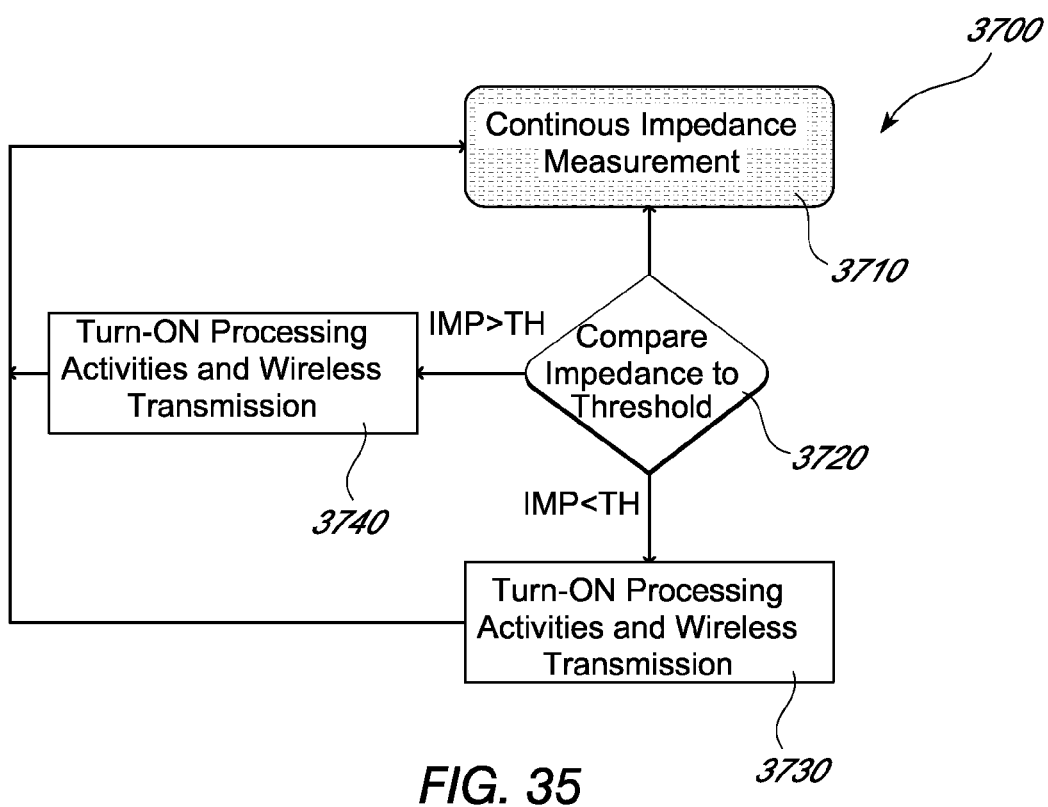
FIG. 35 illustrates a flow chart for turning on and off a monitoring device of which the ASP in accordance with one embodiment forms a part.

FIG. 35 illustrates a flow chart 3700 for turning on and turning off of a monitoring device in accordance with one embodiment. Here, the continuous impedance measurement of ECG signals using the continuous-time impedance monitoring channel 3640 (FIG. 34) is used to initiate activation of the device. The measured impedance, block 3710, is compared to a threshold value in block 3720. If the impedance value is greater than the threshold, the device is turned on and processing activities and wireless transmission can occur, block 3730. If the impedance value is greater than the threshold value, then the device is turned off and processing activities and wireless transmission are disabled, block 3740.

Figure 36:
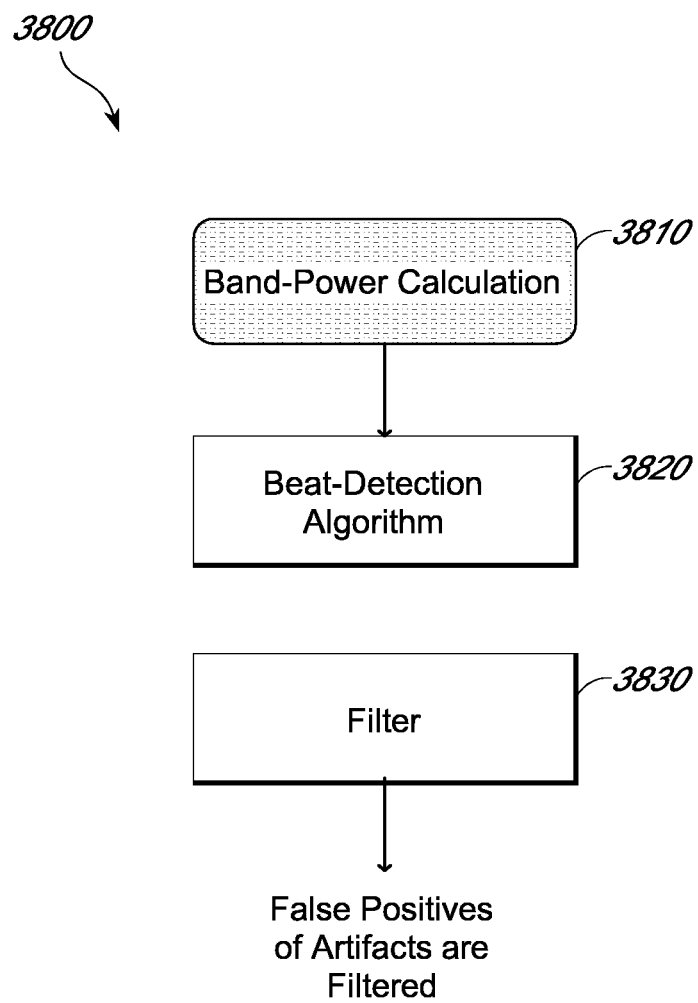
FIG. 36 illustrates a flow chart of a first embodiment for the determination of beat detection.

In FIG. 36, a flow chart 3800 for beat detection in a monitoring device in accordance with one embodiment is shown. The output from a band power calculation, block 3810, is used as the input to a beat-detection algorithm 3820. The output of the beat-detection algorithm 3820 is filtered, block 3830, to remove false positives that are created by artifacts present in the ECG signal.

Figure 37:
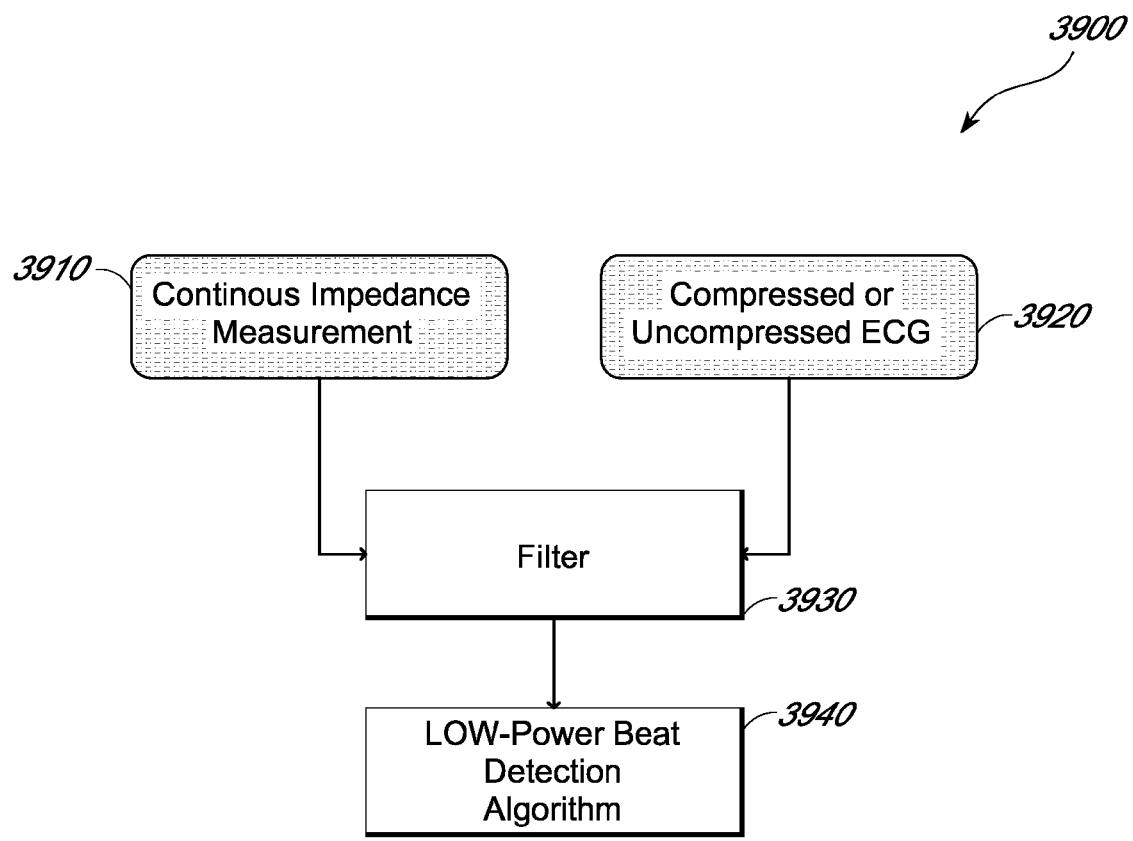
FIG. 37 illustrates a flow chart for the removal of artifacts from an ECG signal.

FIG. 37 illustrates a flow chart 3900 for the removal of artifacts from the ECG signal. Here, the measured impedance, block 3910, and the ECG signal, block 3920 (either in compressed or uncompressed form), are passed to a filter 3930. Artifacts present in the ECG signal are removed using the impedance measurement in the filter, block 3930. The output from the filter is then passed to a low-power beat detection algorithm, block 3940, where beat detection is carried out on the filtered ECG signal.

Figure 38:
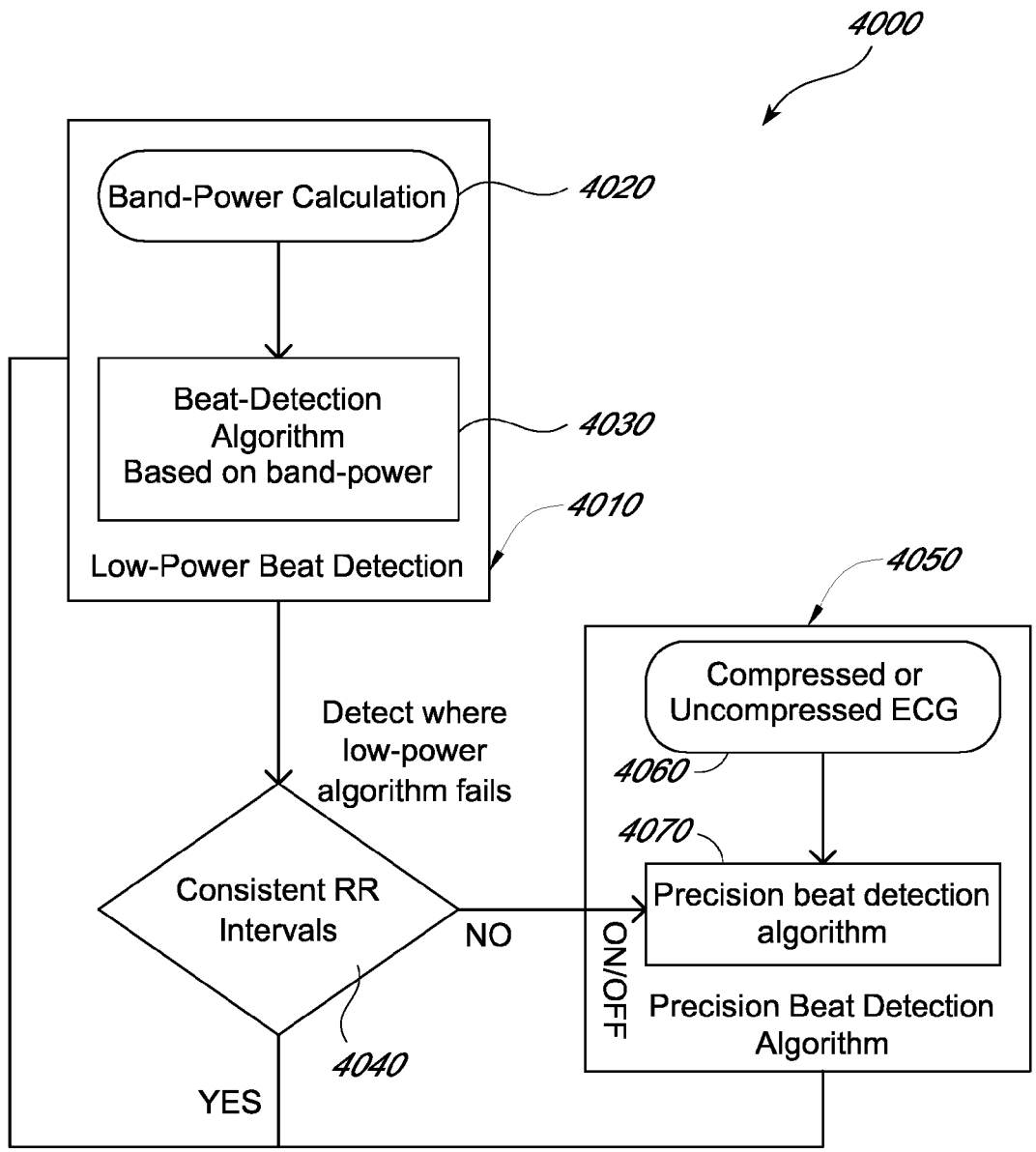
FIG. 38 illustrates a flow chart for a second embodiment for beat detection that compensates for inconsistent determination of the RR interval in an ECG signal.

In FIG. 38, a flow chart 4000 for beat detection using a monitoring device in accordance with one embodiment is shown. Here, two algorithms are used for beat detection. The first algorithm is low-power beat detection, block 4010, which uses the band-power calculation, block 4020, as an input to a beat-detection algorithm based on band power, block 4030. This provides an output signal that is tested for a consistent RR interval determination, block 4040. The second algorithm is a precise beat detection algorithm, block 4050, which is activated when the RR interval determination is inconsistent. For this algorithm, the ECG signal, block 4060, either compressed as described with reference to FIG. 35 above or not, is applied to a precise beat detection algorithm, block 4070. The precision beat detection algorithm, block 4070, is activated when block 4040 determines that the RR interval determination is not consistent so that a more consistent and/or accurate RR interval can be determined. [The RR interval is discussed above with reference to FIGS. 13 and 20.]

If the RR interval is consistently being determined, then the low-power beat detection of block 4010 is used alone. However, if the RR interval is not consistently determined, an indication that the low-power beat detection algorithm is failing, then the precision beat detection algorithm, block 4050, is also used. A negative signal from block 4040 is used to activate the precise beat detection algorithm 4070 as shown. When the determination of the RR interval returns to being consistently determined, the precise beat detection algorithm 4070 is deactivated.

Figure 39:
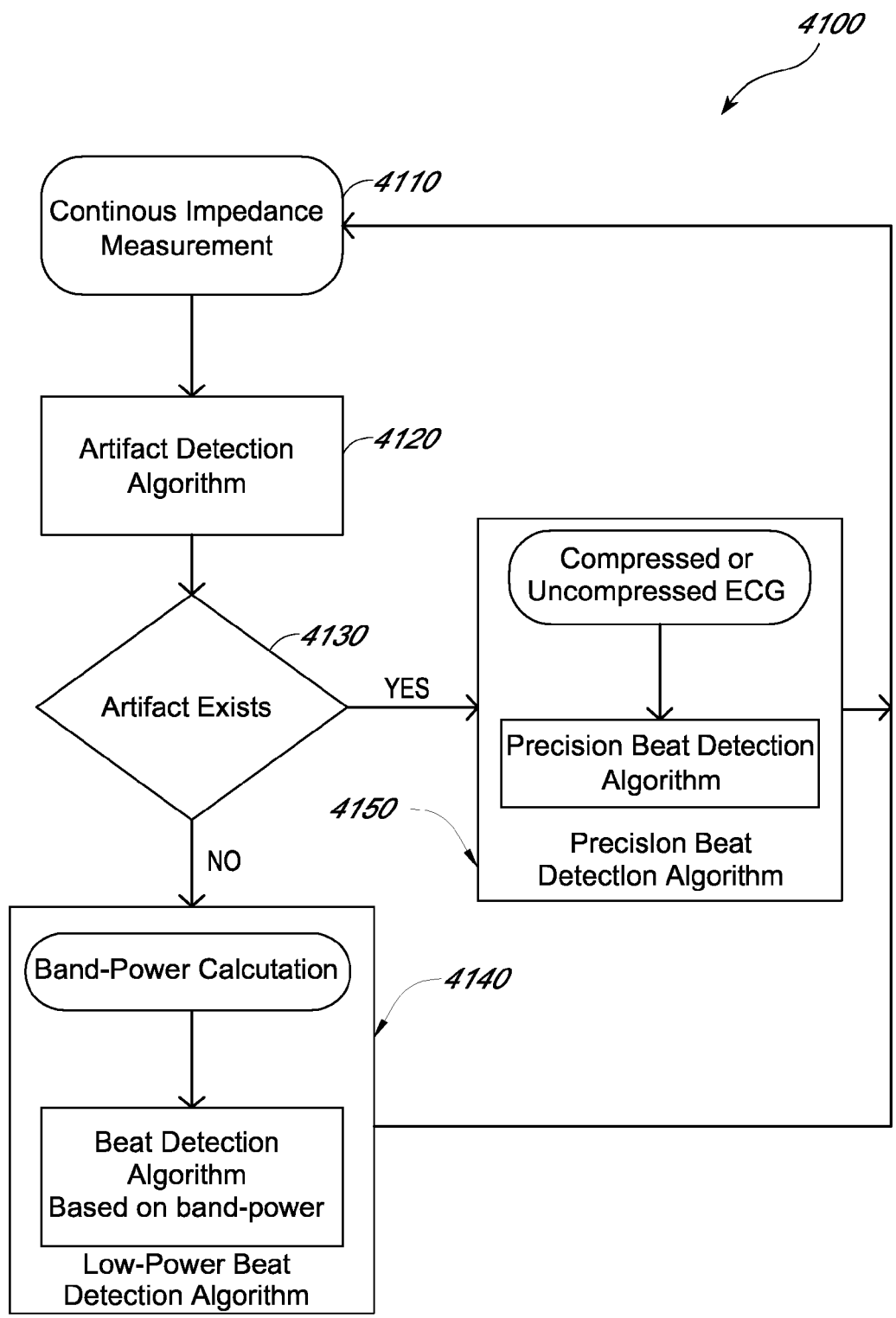
FIG. 39 illustrates a flow chart for a third embodiment for beat detection that compensates for the presence of motion artifacts.

FIG. 39 illustrates a flow chart 4100 in which continuous impedance measurement is used in conjunction with the low-power beat detection algorithm and the precision beat detection algorithm. Here, an impedance measurement, block 4110, is determined from continuous-time impedance monitoring channel 3640 (FIG. 34). An artifact detection algorithm, block 4120, is used to determine in a motion artifact is present. If an artifact does not exist, block 4130, the low-power beat detection algorithm 4140, as described above, is used for the determination of the beats in the input ECG signal. If an artifact exists, block 4130 activates the precision beat detection algorithm 4150 as described above with reference to FIG. 38. When an artifact is not detected, the precision beat detection algorithm is deactivated.

The detection of the presence of motion artifacts using the impedance monitoring allows switching between the low-power beat detection algorithm and the precision beat detection algorithm.

It will be appreciated that the precise beat detection algorithm uses more power than the low-power beat detection algorithm and a substantial amount of power can be saved if the low-power beat detection algorithm is used. As described above, the precise beat detection algorithm is only used where there is inconsistency, for example, inconsistency in the detection of the RR interval, or the presence of artifacts that may lead to false positives in the low-power beat detection algorithm.

The monitoring device in accordance with one embodiment also controls data transfer from the device to a network (not shown) via a radio or wireless link as described above with reference to FIG. 31.

Figure 40:
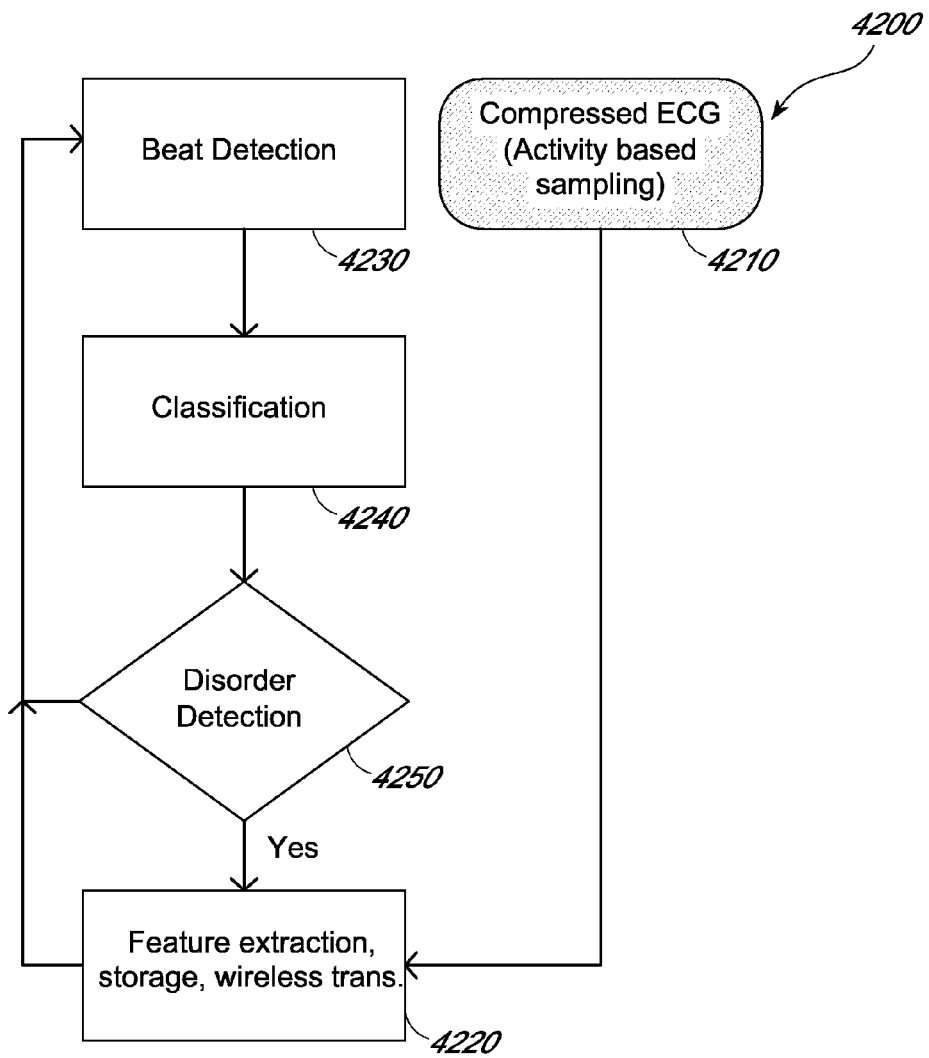
FIG. 40 illustrates a flow chart for a first embodiment for data transfer where a disorder is detected.

In FIG. 40, a flow chart 4200 is shown in which a compressed ECG signal, block 4210, obtained through adaptive sampling as described above, is processed, in block 4220, for feature extraction, storage and/or wireless transmission to a host network (not shown). From block 4220, beat detection is determined in block 4230. The signal is classified, block 4240, and any disorders present detected, block 4250. If no disorders are detected, no action is taken. When a disorder is detected, a signal is transmitted to the host network, block 4220, using a radio or wireless transmission. The occurrence of the disorder can also be stored as a feature of block 4220.

Figure 41:
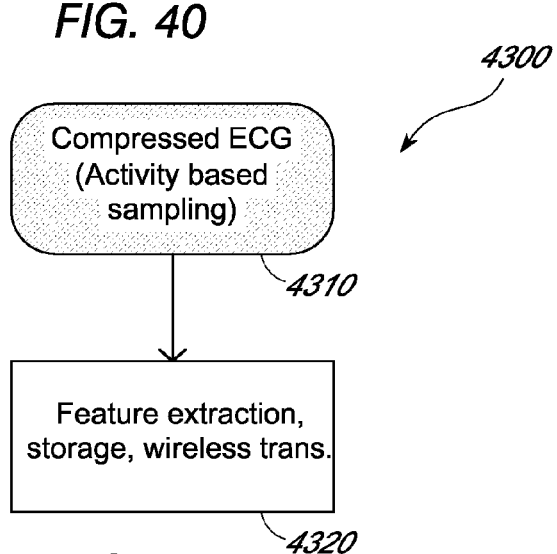
FIG. 41 illustrates a flow chart for a second embodiment for data transfer.

Data transfer can also be carried out continuously as shown in flow chart 4300 in FIG. 41. Here, a compressed ECG signal is obtained through adaptive or activity based sampling, block 4310. The ECG signal is then processed in the back-end processor 3690 (FIG. 34), block 4320. In block 4320, the compressed sampled ECG signal can be stored continuously, processed continuously and/or transmitted wirelessly to the host network.

A monitoring device including the ASP ASIC in accordance with one embodiment can provide:
- The simultaneous measurement of ECG signals and respiration of a subject wearing the monitoring device in order to monitor the autonomic nervous system (ANS) of the subject and to determine ANS responses, energy expenditure, fitness, cardiovascular disease etc.;
- The simultaneous measurement of ECG signals and skin conductance (also known as galvanic skin response (GSR), electrodermal response (EDR), psychogalvanic reflex (PGR), skin conductance response (SCR) or skin conductance level (SCL)) for the measurement of ANS responses;
- The simultaneous measurement of ECG signals, respiration and GSR by extending the number of channels available for subsequent processing;
- The simultaneous measurement of ECG signals and thoracic impedance measurement; and
- The simultaneous measurement of ECG signals and perspiration levels.

The ever increasing cost of healthcare requires a significant improvement in the delivery of healthcare efficiency. Remote monitoring of the patients proposes to tackle this problem, by using portable monitoring systems that have extended battery autonomy. It is especially required that these systems can perform reliable measurements, they have extended power autonomy, and also they are generic enough for reducing the costs. The ASP ASIC in accordance with one embodiment addresses these constrains of portable ECG monitoring systems.

The adaptive sampling and heterodyne chopper readout enables significant reduction in the overall data rate of the signal, assisting the DSP platforms to minimize their power dissipation yet keeping their generic nature to enable the implementation of different algorithms that can be used for different applications.

The impedance measurement technique described, that is, the use of chopper modulation for implementing impedance measurement circuits, eliminates the requirement for the sinusoidal current generation and reduces the power consumption of the impedance measurement circuits significantly, while enabling continuous time signal integrity monitoring.

As discussed above, the ASP ASIC in accordance with one embodiment merely consume 30 μW from 2V supply and leads to the development of a wireless ECG monitoring system that is more than four times more power efficient than its predecessors and sufficiently generic to allow the implementation of different ECG beat detection algorithms.

Although the present disclosure has been described with reference to cardiac monitoring, it will be appreciated that it can also be used for the monitoring of other vital signs where adaptive sampling of the monitored sign is required. Moreover, an ASP ASIC may also be used for other applications where adaptive sampling of a signal is required.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

While the above detailed description has shown, described, and pointed out novel features of the disclosure as applied to various embodiments, it will be understood that various omissions, substitutions, and changes in the form and details of the device or process illustrated may be made by those skilled in the technology without departing from the spirit of the disclosure. The scope of the invention is indicated by the appended claims rather than by the foregoing description. All changes which come within the meaning and range of equivalency of the claims are to be embraced within their scope.

What is claimed is:

1. An application-specific integrated circuit for cardiac monitoring, the circuit comprising:
   an electrocardiogram readout channel having an input and an output, the input being arranged to receive a monitored signal and the output providing an electrocardiogram signal;
   an impedance readout channel configured to extract impedance information from the monitored signal; and
   an adaptive sampling unit configured to sample the electrocardiogram signal output by the electrocardiogram readout channel, the adaptive sampling unit comprising
      an adaptive threshold generation unit configured to generate a threshold value which is used to control the adaptive sampling unit,
      an activity detector which comprises a switched capacitor differentiator configured to sense the rate of change of the electrocardiogram signal and to provide an output indicative thereof,
      a comparator configured to compare the output from the switched capacitor differentiator with the threshold value, and
      a selector configured to select between a low sampling rate and a high sampling rate in accordance with the comparison.

2. The application-specific integrated circuit according to claim 1, wherein the adaptive threshold generation unit forms part of a negative feedback loop in which the output from the comparator is filtered to provide one input to a further comparator within the adaptive threshold generation unit, the other input to the further comparator being calculated from heart rate information.

3. The application-specific integrated circuit according to claim 2, wherein the threshold value is regulated to match the input of the further comparator to the duty cycle of the comparator.

4. The application-specific integrated circuit according to claim 1, further comprising a band-power extraction channel configured to extract power information from the monitored signal.

5. The application-specific integrated circuit according to claim 4, further comprising a digital control circuit supplying frequency and control signals for the electrocardiogram readout channel, the band-power extraction channel, and the impedance readout channel.

6. The application-specific integrated circuit according to claim 5, wherein the digital control circuit receives inputs from two low frequency oscillators and one high frequency oscillator.

7. The application-specific integrated circuit according to claim 1, further comprising an input stage configured to provide the monitored signal to at least the electrocardiogram readout channel.

8. The application-specific integrated circuit according to claim 1, wherein the impedance readout circuit further comprises a stimulation current generator which provides a chopper-stabilized AC current at an electrode-tissue interface, the resulting voltage therefrom being amplified by the impedance readout channel to extract the electrode-tissue impedance.

9. The application-specific integrated circuit according to claim 1, further comprising at least one output stage.

10. The application-specific integrated circuit according to claim 1, wherein the adaptive sampling unit comprises an analogue-to-digital converter.

11. A medical monitoring device comprising:
the application-specific integrated circuit according to claim 1;
a digital controller configured to process signals output by the application-specific integrated circuit and to provide control signals to the application-specific integrated circuit; and
a wireless module configured to receive data from the digital controller and to transmitting it to a network.

12. A wireless electrocardiogram monitoring system comprising:
a network; and
the medical monitoring device according to claim 11, wherein the wireless module of the medical monitoring device is configured to transmit data to the network.

13. A method of transferring data from a medical monitoring device according to claim 11, the method comprising:
determining an adaptively sampled ECG signal;
processing the adaptively sampled ECG signal to extract features therefrom; and
transmitting data relating to the extracted features to a host network.

14. The method according to claim 13, wherein data is transferred continuously.

15. The method according to claim 13, wherein data is transferred when a disorder is detected in the extracted features.

* * * * *